United States Patent [19]

Das

[11] Patent Number: 4,734,426
[45] Date of Patent: Mar. 29, 1988

[54] 5,6-EPOXY-7-OXABICYCLOHEPTANE SUBSTITUTED DIAMIDE PROSTAGLANDIN ANALOGS

[75] Inventor: Jagabandhu Das, Plainsboro, N.J.

[73] Assignee: E. R. Squibb & Sons, Inc., Princeton, N.J.

[21] Appl. No.: 911,178

[22] Filed: Sep. 24, 1986

[51] Int. Cl.$^4$ .................. C07D 493/18; A61K 31/34; A61K 31/41
[52] U.S. Cl. .................................... 514/382; 514/468; 548/253; 549/459
[58] Field of Search .................... 549/459; 548/253; 514/382, 468

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,416,896 | 11/1983 | Nakane et al. | 424/285 |
| 4,456,615 | 6/1984 | Nakane et al. | 424/285 |
| 4,456,617 | 6/1984 | Nakane et al. | 424/285 |
| 4,609,671 | 9/1986 | Das | 514/468 |
| 4,611,005 | 9/1986 | Das | 514/468 |
| 4,611,006 | 9/1986 | Das | 514/468 |

FOREIGN PATENT DOCUMENTS 0043292 8/1982 European Pat. Off. .
0082646 6/1983 European Pat. Off. .
2039909 8/1980 United Kingdom .

Primary Examiner—Robert Gerstl
Attorney, Agent, or Firm—Lawrence S. Levinson; Burton Rodney

[57] ABSTRACT 5,6-Epoxy-7-oxabicycloheptane substituted diamide prostaglandin analogs are provided having the structural formula

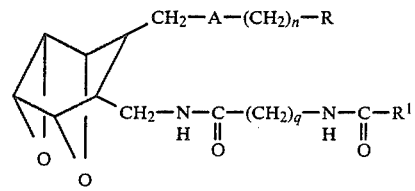

wherein A is —CH=CH— or —CH$_2$—CH$_2$—; n is 1 to 5; R is CO$_2$H, CO$_2$alkyl, CO$_2$alkali metal, CO$_2$polyhydroxyamine salt or

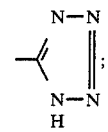

q is 1 to 12; and R$^1$ is H, lower alkyl, lower alkenyl, lower alkynyl, aryl, arylalkyl, lower alkoxy, aryloxy, arylalkyloxy, amino, alkylamino arylamino, arylalkylamino, lower alkyl—S$\overset{(O)_{n'}}{\underset{\parallel}{}}$—, aryl—S$\overset{(O)_{n'}}{\underset{\parallel}{}}$—, arylalkyl—S$\overset{(O)_{n'}}{\underset{\parallel}{}}$—, aryl—S$\overset{(O)_{n'}}{\underset{\parallel}{}}$—alkyl—, alkyl—S$\overset{(O)_{n'}}{\underset{\parallel}{}}$—alkyl—, arylalkyl—S$\overset{(O)_{n'}}{\underset{\parallel}{}}$—alkyl (wherein n' is 0, 1 or 2), alkylaminoalkyl, arylaminoalkyl, arylalkylaminoalkyl, alkoxyalkyl, aryloxyalkyl or arylalkoxyalkyl.

The compounds are cardiovascular agents useful, for example, in the treatment of thrombotic disease.

21 Claims, No Drawings

5,6-EPOXY-7-OXABICYCLOHEPTANE SUBSTITUTED DIAMIDE PROSTAGLANDIN ANALOGS

DESCRIPTION OF THE INVENTION

The present invention relates to 5,6-epoxy-7-oxabicycloheptane substituted diamide and congener prostaglandin analogs which are cardiovascular agents useful, for example, in the treatment of thrombotic disease. These compounds have the structural formula

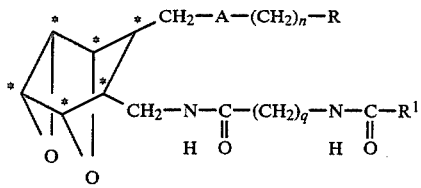   I including all stereoisomers thereof, wherein A is —CH=CH— or —CH$_2$—CH$_2$—; n is 1 to 5; R is CO$_2$H, CO$_2$alkyl, CO$_2$ alkali metal, CO$_2$polyhydroxyamine salt, or

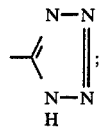;

q is 1 to 12; and R$^1$ is lower alkyl, lower alkenyl, lower alkynyl, aryl, arylalkyl, lower alkoxy, arylalkyloxy, aryloxy, alkylamino, arylalkylamino, arylamino,

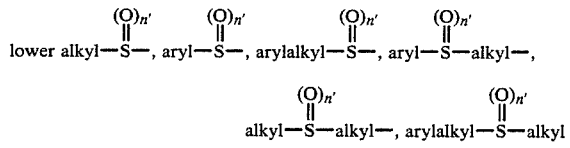

(wherein n' is 0, 1 or 2), alkylaminoalkyl, arylaminoalkyl, arylalkylaminoalkyl, alkoxyalkyl, aryloxyalkyl or arylalkoxyalkyl.

The term "lower alkyl" or "alkyl" as employed herein alone or as part of another group includes both straight and branched chain hydrocarbon, containing 1 to 12 carbons in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkylaryl substituent, a haloaryl substituent, a cycloalkyl substituent, an alkylcycloalkyl substituent, hydroxy, and alkylamino substituent, an alkanoylamino substituent, an arylcarbonylamino substituent, a nitro substituent, a cyano substituent, a thiol substituent or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy", or "aryloxy" or "aralkoxy" as employed herein alone or as part of another group includes any of the above lower alkyl, alkyl, aralkyl or aryl groups linked to an oxygen atom.

The term "lower alkylthio", "alkylthio", "arylthio" or "aralkylthio" as employed herein alone or as part of another group includes any of the above lower alkyl, alkyl, aralkyl or aryl groups linked to a sulfur atom.

The term "lower alkylamino", "alkylamino", "arylamino", "arylalkylamino" as employed herein alone or as part of another group includes any of the above lower alkyl, alkyl, aryl or arylalkyl groups linked to a nitrogen atom.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The terms (CH$_2$)$_n$ includes straight or branched chain radicals having from 1 to 5 carbons in the normal chain and may contain one or more lower alkyl and/or halogen substituents. Examples of (CH$_2$)$_n$ groups include

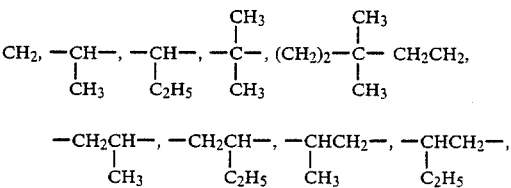

-continued

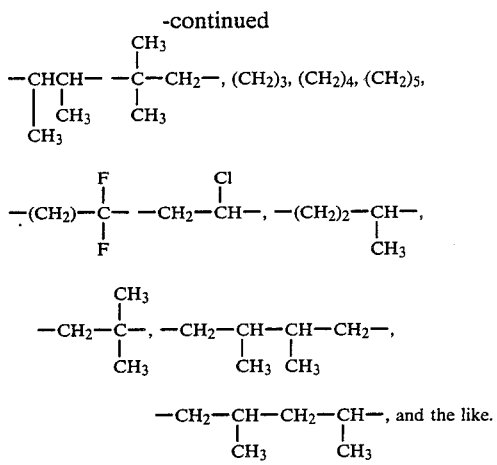

The term $(CH_2)_q$ includes straight or branched chain radicals having from 1 to 12 carbons in the normal chain and includes any of the above examples of $(CH_2)_n$ groups as well as $(CH_2)_6$, $(CH_2)_7$, $(CH_2)_8$, $(CH_2)_9$, $(CH_2)_{10}$, $(CH_2)_{11}$, $(CH_2)_{12}$, and may be unsubstituted or substituted by one or more halo, hydroxy, alkoxy, amino, alkylamino, arylamino, amido, thioamido, thiol, alkylthio, arylthio, cyano or nitro groups.

The term "amido" refers to the group

wherein $R^2$ and $R^3$ are independently hydrogen, lower alkyl or aryl.

The term "polyhydroxyamine salt" refers to glucamine salt or tris(hydroxymethyl)aminomethane.

The term "halogen" or "halo" as used herein refers to chlorine, bromine, fluorine, iodine and $CF_3$, with chlorine or fluorine being preferred.

Preferred are those compounds of formula I wherein A is a —CH=CH—, n is 1 or 4, R is $CO_2H$, $(CH_2)_q$ is —$CH_2$—; and $R^1$ is lower alkyl, such as pentyl, hexyl, or heptyl or lower alkoxy, such as pentoxy, lower alkylamino such as pentylamino or arylthioalkyl, such as phenylthiomethyl.

The compounds of formula I of the invention may be prepared as described below.

A. $R^1$ is H

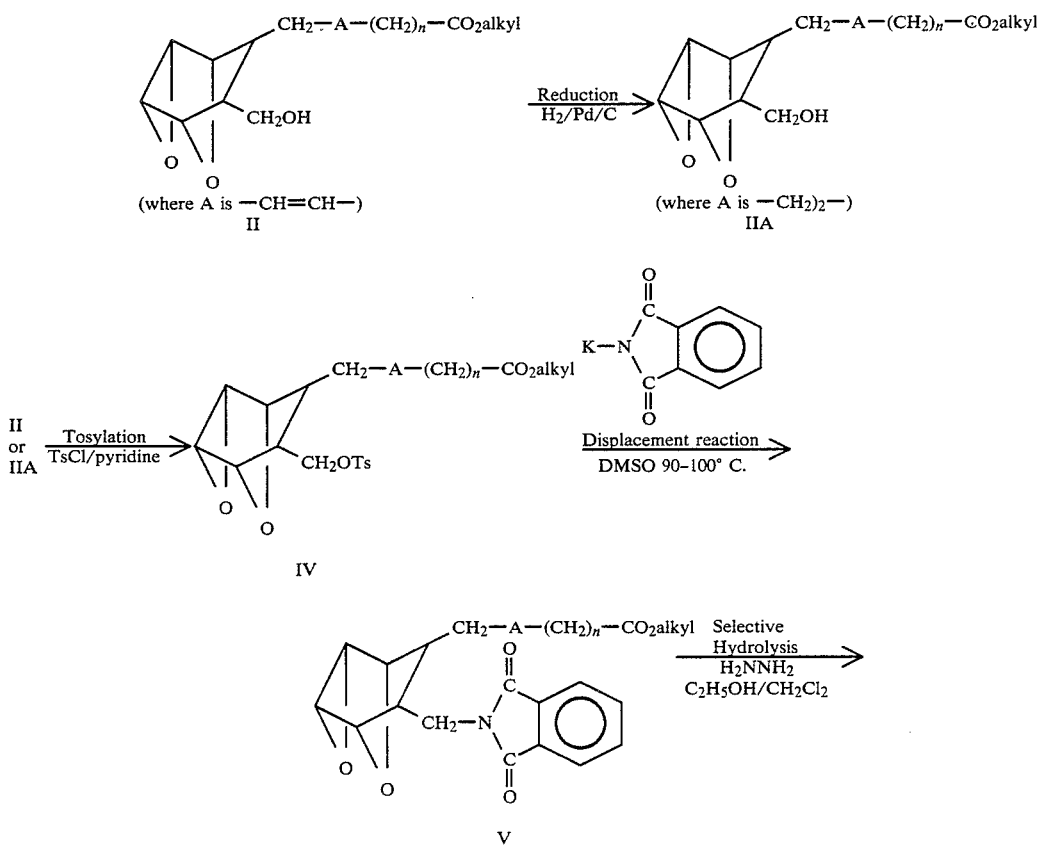

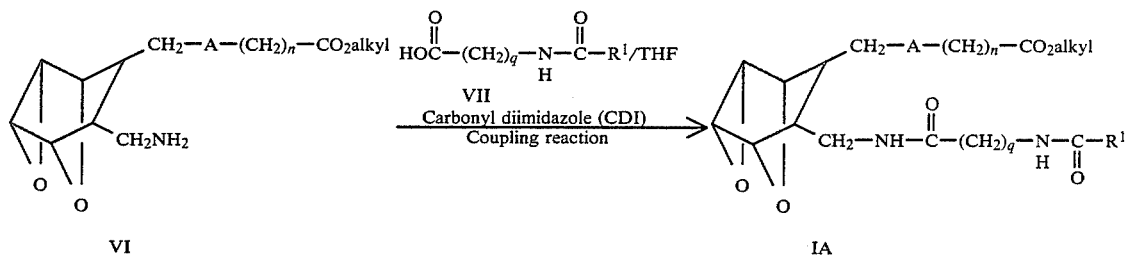
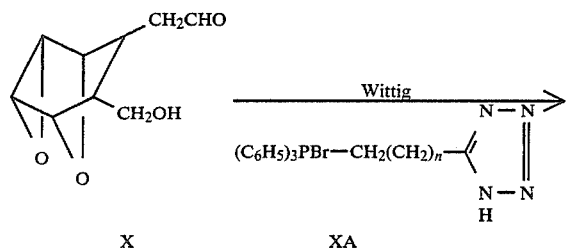
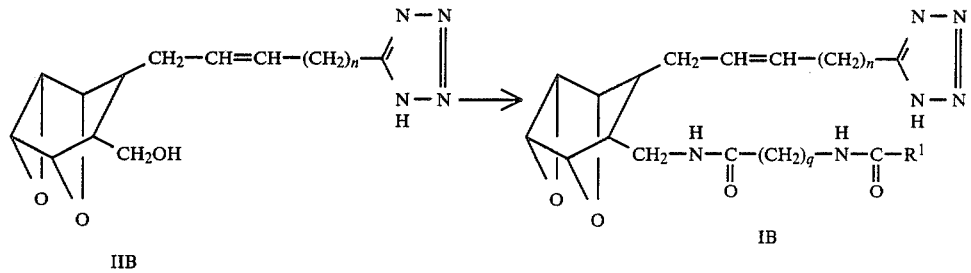
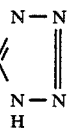
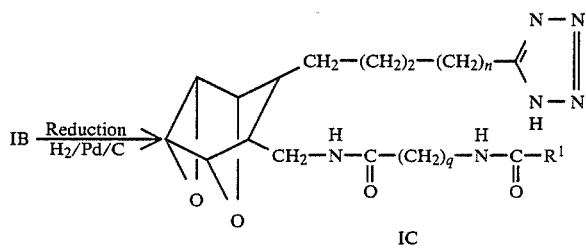
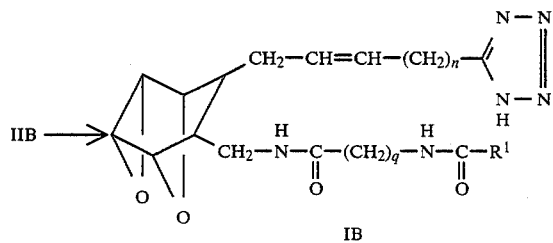

C. Where R is 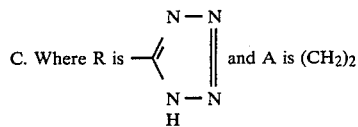 and A is $(CH_2)_2$

IB $\xrightarrow[H_2/Pd/C]{\text{Reduction}}$ 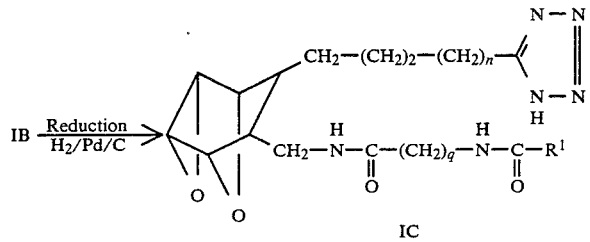
IC

As seen in reaction sequence "A", compounds of the invention where R is $CO_2$alkyl, that is

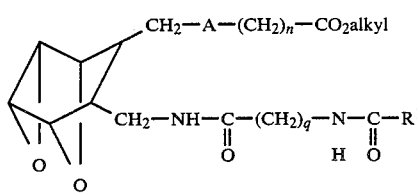
IA are prepared by tosylating the lower alkyl ester containing the hydroxymethyl group, that is, compound II or IIA, (prepared as described in U. S. Pat. No. 4,143,054) by reacting II or IIA with tosyl chloride in the presence of pyridine to form the corresponding tosylate IV which is subjected to a displacement reaction by dissolving IV in dimethylsulfoxide and heating to 90° to 100° C. in the presence of potassium phthalimide to form the phthalimide V. The phthalimide V is then made to undergo selective hydrolysis by dissolving V in methylene chloride and ethanol under an inert atmosphere such as argon and reacting with anhydrous hydrazine to form the amine VI

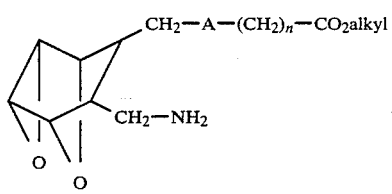
VI

The amine VI is then subjected to a CDI coupling reaction by reacting VI with acid VII

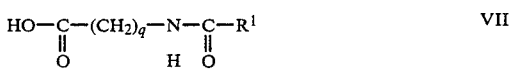
VII in the presence of an inert organic solvent such as tetrahydrofuran and carbonyl diimidazole under an inert atmosphere, such as argon, employing a molar ratio of VI:VII of within the range of from about 1.1 to about 1:1.2, to form the amide ester compound of the invention IA.

Compounds of the invention wherein R is

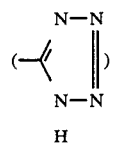

and A is CH=CH are prepared as described in reaction sequence "B" wherein alcohol X

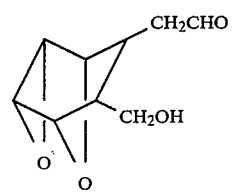
X (prepared by treatment of compound L with aqueous acid) is reacted with a Wittig reagent of the structure XA

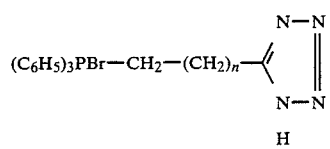
XA in the presence of a base, such as potassium t-butoxide or sodium hydride-dimethyl sulfoxide employing a molar ratio of X:XA of within the range of from about 1:1 to about 0.2:1 to form the hydroxymethyl compound IIB

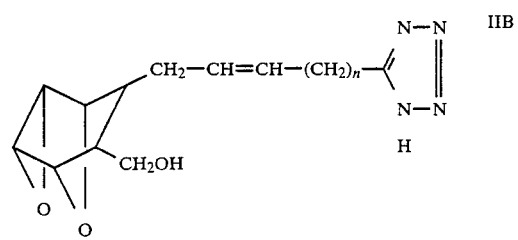
IIB which may then be employed in reaction sequence "A" in place of compound II or IIA to form compounds of the invention IB where A is —CH=CH— or IC where A is (CH₂)₂

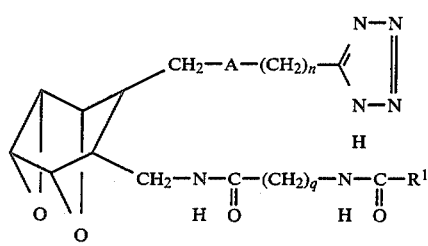

IB or IC

Alternatively, compound IC may be prepared by reducing compound IB by treating with H₂ in the presence of palladium on charcoal.

Referring to reaction sequence "A", the ester IA can be converted to the free acid, that is, to

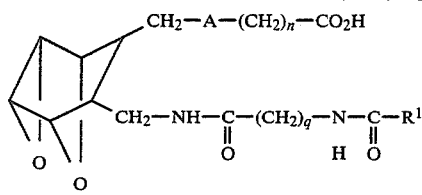

ID (A is —CH=CH—)
IE (A is (CH₂)₂)

by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention ID and IE.

The starting compound II may be prepared as outlined below.

Dione having the structure A

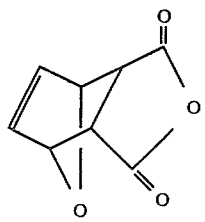

A that is, 7-oxabicyclo[2.2.1]-5-heptene-2,3-dicarboxylic anhydride [Ber. 62, 554 (1920); Ann. 460, 98 (1928)] is reduced, for example, by reacting with lithium aluminum hydride or diisobutyl aluminum hydride in the presence of an inert organic solvent such as tetrahydrofuran, ether or toluene at reduced temperatures of from about −78° C. to about 67 ° C. to form diol B of the structure

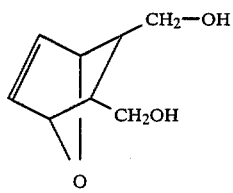

B

The diol B is subjected to a chloroformylation reaction by reacting B dissolved in an inert organic solvent as described above, with phosgene in the presence of a solvent such as tetrahydrofuran, toluene, benzene or xylene, to form an alcohol of the structure

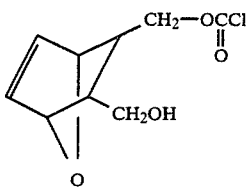

C

The alcohol C is dissolved in an inert organic solvent such as methylene chloride, tetrahydrofuran or ether and then reacted with an organic base, such as pyridine, triethylamine, N,N-dimethylaminopyridine or diazabicycloundecane (DBU) at reduced temperatures of from about −78° C. to about 25° C., to form cyclic carbonate D

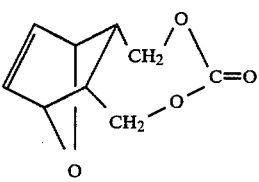

D

The cyclic carbonate D is then subjected to alcoholysis by reacting D with an alkanol (alkyl-OH) having from 1 to 12 carbons, such as ethanol, n-propanol, isopropanol, butanol, pentanol, hexanol, heptanol, octanol, nonenol or decanol, including all the various isomers thereof, preferably isopropyl alcohol, employing a molar ratio of D: alkanol of within the range of from about 1:10 to about 1:100 to form hydroxycarbonate E

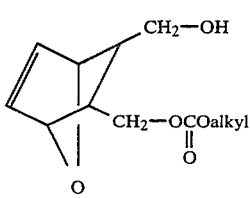

E (wherein alkyl contains 1 to 12 carbons as defined herein).

Thereafter, the hydroxy carbonate E is tosylated (or otherwise protected) by reacting E (dissolved in methylene chloride, and a basic solvent such as pyridine, triethylamine or dimethylaminopyridine) with tosyl chloride or other protecting agent, such as methane sulfonyl chloride (mesyl chloride) and trifluoromethanesulfonic anhydride, to form the tosylate F or other protected compound

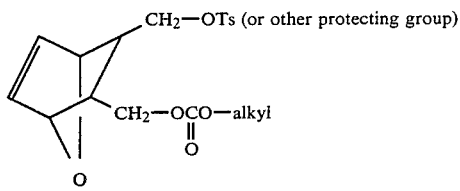

Then, the tosylate F dissolved in an inert solvent such as dimethylsulfoxide, or dimethylformamide is cyanated by reacting F with an alkali metal cyanide such as NaCN or KCN employing a molar ratio of IV:cyanide of within the range of from about 1:1 to about 10:1, at elevated temperatures of from about 80° C. to about 130° C., in an inert atmosphere, such as an argon atmosphere, to form the cyanocarbonate G

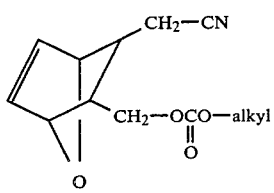

Cyanocarbonate G is dissolved in an alcohol such as methanol or ethanol and treated with aqueous alkali metal carbonate such as potassium carbonate at reduced temperature to form cyano-alcohol H

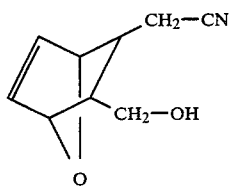

which is made to undergo tetrahydropyranyl ether formation by reacting cyano alcohol H with dihydropyran in the presence of an inert organic solvent such as methylene chloride or ether and catalytic amount of p-toluene sulfonic acid at reduced temperatures of from about 0° C. to about 10° C., to form the tetrahydropyranyl ether of formula J

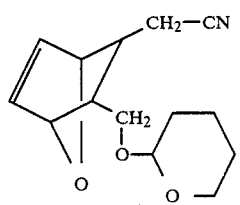

Compound J is then made to undergo epoxide formation by treating a solution of J in methylene chloride or other appropriate solvent with m-chloroperoxybenzoic acid at reduced temperatures to form epoxy nitrile K

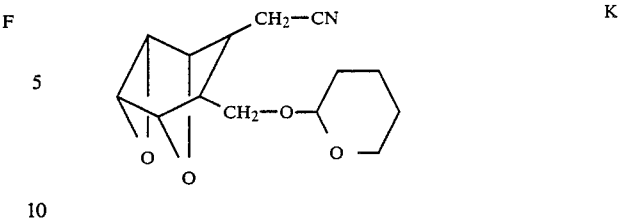

The compounds of formula II may be formed starting with compound K in accordance with the following.

Compound K is treated with diisobutyl aluminum hydride (DIBALH) in the presence of an inert solvent such as toluene or tetrahydrofuran at reduced temperatures of from about −70° to about −85° C. to form epoxy aldehyde L

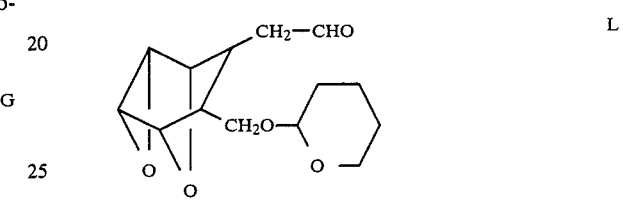

Epoxy aldehyde L in appropriate solvent such as tetrahydrofuran is then reacted with a suspension formed by mixing dry carboxyalkyltriphenylphosphonium halide M

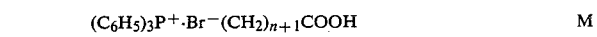

in tetrahydrofuran with potassium t-amylate in toluene at reduced temperature and the reaction product treated with ethereal diazoalkane to form the ester N

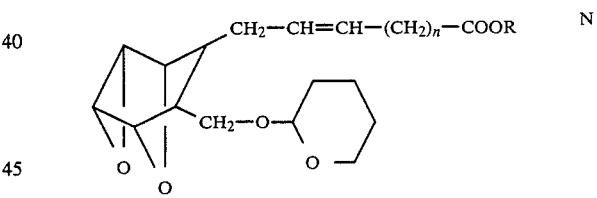

(wherein R is lower alkyl).

Compound N is dissolved in methanol and is then hydrolyzed by treatment with strong acid such as HCl, Amberlyst resin or acetic acid to form alcohol II.

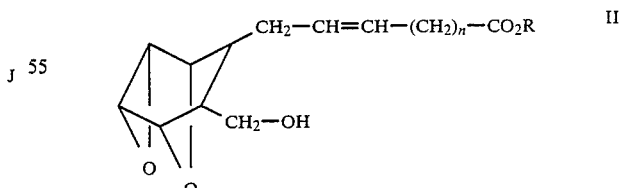

(wherein R is lower alkyl).

The tris(hydroxymethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

To form the sulfinyl and/or sulfonyl analogs of compounds of formula I wherein $R^1$ is -S-alkyl, -S-aryl, -S-alkylaryl, -alkyl-S-aryl, alkyl-S-alkyl, or -alkyl-S-alkylaryl, such formula I compounds are subjected to oxidation, for example, by reacting same with sodium periodate or potassium monopersulfate (oxone) in the presence of methanol to form the sulfinyl derivative and/or sulfonyl derivative. Mixtures thereof may be separated by chromatography or other conventional separation procedures.

The starting acid VII

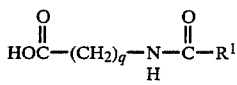

VII may be prepared by reacting the amino acid VIIA

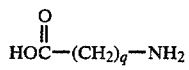

VIIA or its acid chloride with acid chloride VIIB

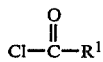

VIIB (or its acid if the acid chloride of VIIA is employed) in the presence of a strong base such as NaOH and water.

The compounds of this invention have six centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cisendo and all trans forms and stereoisomeric pairs may be prepared as shown in the working Examples which follow and by employing starting materials following the procedures as outlined in U. S. Pat. No. 4,143,054. Examples of such stereoisomers are set out below.

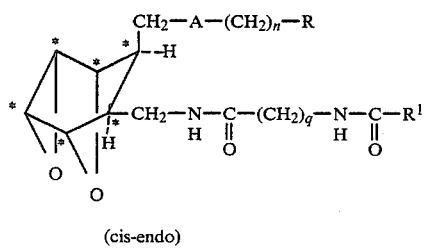

(cis-endo) Ia

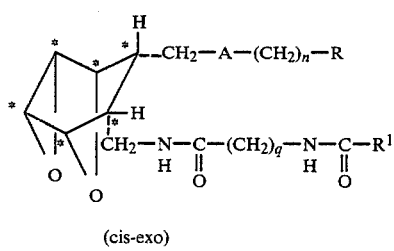

(cis-exo) Ib

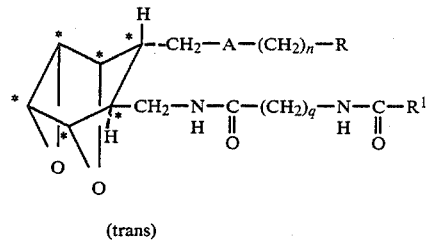

(trans) Ic

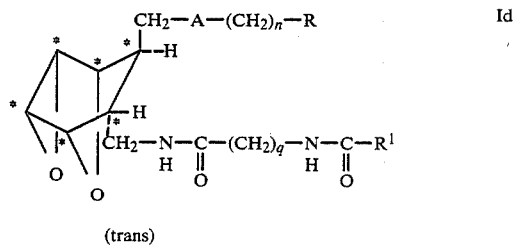

(trans) Id

The nucleus in each of the compounds of the invention is depicted as

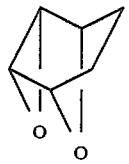

for matter of convenience; it will also be appreciated that the nucleus in the compounds of the invention may be depicted as

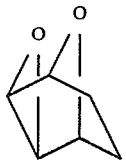

The compounds of this invention are cardiovascular vascular agents useful as platelet aggregation inhibitors, such as in inhibiting arachidonic acid-induced platelet aggregation, e.g., for treatment of thrombotic disease such as coronary or cerebral thromboses, and in inhibiting bronchoconstriction. constriction. They are also selective thromboxane $A_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cattle, horses, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1α,2β(5Z),3β,4α,5α,6α]-7-[5,6-Epoxy-3-[[[[(1-oxohexyl)amino]acetyl]amino]methyl]-7-oxabicyclo[2.2.1-]hept-2-yl]-5-heptenoic acid, methyl ester A. [1α,2β(5Z),3β,4α,5α,6α]-7-[5,6-Epoxy-3-hydroxymethyl-7-oxabicyclo[2.2.1]hept-2-yl]-5-heptenoic acid, methyl ester A(1) 7-Oxabicyclo[2.2.1]-5-hepten-2,3-dimethanol To a suspension of 6.84 g of lithium aluminum hydride (180 mmol) in 200 ml of freshly distilled THF, cooled in an ice-water bath was added dropwise, a solution of 20 g of 7-oxabicyclo[2.2.1]-5-heptene-2,3-dicarboxylic anhydride (120 mmol) in 150 ml of dry THF, over a period of 1 hour. After the addition, the cooling bath was removed and the reaction mixture was stirred at room temperature for 24 hours. The reaction mixture was now cooled in an ice-water bath and excess of hydride was destroyed by slow addition of freshly prepared saturated sodium sulfate solution. Addition was continued until all the inorganic salts were precipitated as white granular solids. Anhydrous magnesium sulfate was added to the reaction mixture and it was filtered. The residue was thoroughly washed with methylene chloride. The residue was taken up in 500 ml of 10% acetonitrile in ethyl acetate, stirred for 30 minutes and finally was filtered. The combined filtrate was concentrated under reduced pressure. The crude residue was chromatographed on a silica gel column. Elution with 50% ethyl acetate in hexane, followed by ethyl acetate and finally with 10% methanol in ethyl acetate afforded 17.25 g of title diol as a colorless viscous oil.

A(2) 7-Oxabicyclo[2.2.1]-5-heptene-2,3-dimethanol carbonate

To a solution of 16.73 g of Part A(1) diol (107.4 mmole) in 200 ml of freshly distilled THF, cooled in an ice-water bath was added dropwise 90 ml of a 12.5% by weight solution of phosgene in toluene (112.5 mmol), over a period of 45 minutes. The reaction mixture was stirred for an additional 15 minutes, whereupon argon was bubbled through to remove excess of phosgene and hydrogen chloride formed during the reaction. The reaction mixture was now concentrated under reduced pressure. The crude monochloroformate was now dissolved in 250 ml of methylene chloride and cooled at −50° C. in a dry ice-acetone bath. A solution of 25 ml of pyridine in 50 ml of methylene chloride was now added dropwise over a period of 20 minutes. An immediate white precipitate was formed upon addition. The reation mixture was left at −50° C. for an additional 30 minutes, whereupon the cooling bath was removed and the reaction mixture was washed thoroughly with water. The methylene chloride layer was dried over anhydrous magnesium sulfate, filtered and the filtrate was concentrated under reduced pressure. The crude residue was triturated with ether, cooled at 0° C. and the precipitated title carbonate was filtered off. 15.25 g of white crystalline title carbonate was obtained.

A(3) 2-Hydroxymethyl-3-isopropyloxycarbonyloxymethyl-7-oxabicyclo[2.2.1]heptene

To a suspension of 15.25 g of Part A(2) cyclic carbonate (83.8 mmole) in 200 ml of isopropyl alcohol was added with stirring 1 g of p-toluene sulfonic acid. The reaction mixture was heated under reflux for 8 hours whereupon it was cooled and isopropanol was removed by distillation under reduced pressure. The crude residue was dissolved in methylene chloride and washed with aqueous sodium bicarbonate solution. The aqueous layer was extracted several times with methylene chloride. The combined methylene chloride extract was dried over anhydrous magnesium sulfate and was then concentrated under reduced pressure to obtain 22.53 g of title isopropyloxycarbonate as a viscous oil.

A(4) 2-p-Toluenesulfonyloxymethyl-3-isopropyloxycarbonyloxymethyl-7-oxabicyclo[2.2.1]heptene To a solution of 22.53 g of Part A(3) isopropyloxycarbonate (84 mmole) in 100 ml of pyridine was added with stirring 19.2 g of p-toluene sulfonyl chloride (101 mmole) at 0°–5° C. The reaction mixture was stirred at room temperature for 24 hours, whereupon it was diluted with methylene chloride and washed thoroughly with water, saturated copper sulfate solution and finally with water. The combined aqueous layer was extracted with two 200 ml portions of methylene chloride. The combined methylene chloride extract was dried over anhydrous magnesium sulfate and finally was concentrated under reduced pressure. The crude residue was triturated with ether, cooled at 0° C. and the precipitate title tosylate (28.3 g) was filtered off. The mother liquor was concentrated and chromatographed on a silica gel column to obtain additional 5.2 g of crystalline title tosylate (eluting solvent 15–30% ethyl acetate in hexane).

A(5) 2-Cyanomethyl-3-isopropyloxycarbonyloxymethyl-7-oxabicyclo[2.2.1]heptene

To a solution of 5.3 g of Part A(4) tosylate (12.99 mmole) in 50 ml of dry dimethylsulfoxide was added with stirring 1.28 g of powdered sodium cyanide (26 mmole). The reaction mixture was placed on an oil bath (bath temperature 90°–95° C.) and heated for 2 hours. It was now cooled and diluted with 200 ml of ether. The reaction mixture was now thoroughly washed with water. The combined aqueous extract was extracted with two 150 ml of ether. The ether layer was now dried over anhydrous magnesium sulfate and concentrated under reduced pressure. The crude residue was chromatographed on a silica gel column. Elution with 25–50% ehtyl acetate in hexane afforded 2.58 g of title cyano-carbonate.

A(6) 2-Cyanomethyl-3-hyroxymethyl-7-oxabicyclo[2.2.1]heptene

To a solution of 1 g of potassium carbonate in 25 ml of water and 75 ml of methanol, cooled in an ice-water bath was added with stirring a solution of 2.58 g of Part A(5) cyano-carbonate (9.8 mmol) in 10 ml of methanol. After 15 minutes, the cooling bath was removed and the reaction mixture was allowed to stand at room temperature for additional 6 hours, whereupon it was acidified with 1N aqueous hydrochloric acid solution. Most of methanol was now removed by distillation under reduced pressure. The residue was now exhaustively extracted with methylene chloride (X12) (after saturating it with sodium chloride). The combined organic extract was dried over anhydrous magnesium sulfate and concentrated under reduced pressure. The crude residue was chromatographed on a silica gel column and eluted with 25–50% ethyl acetate in hexane, followed by ethyl acetate to obtain 1.23 g of title cyano alcohol.

A(7) 2-Cyanomethyl-3-tetrahydropyranyloxymethyl-7-oxabicyclo[2.2.1]heptene

A solution of 1.23 g of Part A(6) cyano-alcohol (7.36 mmole) in 20 ml of dry methylene chloride was treated with 800 ml of dihydropyran (8.89 mmole) and catalytic amount of p-toluene sulfonic acid at 0°–5° C. After 4 hours, the reaction mixture was diluted with ether and washed with aqueous sodium bicarbonate solution. The aqueous layer was reextracted twice with ether. The combined organic extract was dried over anhydrous magnesium sulfate and concentrated under reduced pressure. The crude residue was chromatographed on a silica gel column and eluted with 20–25% ethyl acetate in hexane to obtain 1.61 g of title tetrahydropyranyl ether.

A(8) 5,6-Epoxy-2-cyanomethyl-3-tetrahydropyranyloxymethyl-7-oxabicyclo[2.2.1]heptene A solution of 1.61 g of Part A(7) cyano ether (6.4 mmole) in 20 ml of dry methylene chloride was treated with 1.66 g of 80% pure m-chloroperoxybenzoic acid (9.6 mmole) at 0°–5° C. After a few minutes, the cooling-bath was removed and the reaction mixture was let stand at room temperature for 6 hours. The reaction mixture was now diluted with ether and excess of per-acid was decomposed by addition of aqueous sodium meta-bisulfite solution. After stirring for 30 minutes, the organic layer was separated and the aqueous layer was extracted twice with methylene chloride. The combined organic extract was dried over anhydrous magnesium sulfate and concentrated under reduced pressure. Purification by chromatography on a silica gel column (eluting solvent 25–67% ethyl acetate in hexane) afforded 1.57 g of title epoxide.

A(9) 5,6-Epoxy-2-formylmethyl-3-tetrahydropyranyloxymethyl-7-oxabicyclo[2.2.1]heptane To a solution of Part A(8) epoxy-nitrile (1.57 g, 5.88 mmole) in 25 ml of toluene, cooled at $-78°$ C. in a dry ice-acetone bath was added with stirring, 6.8 ml of a 25% by weight solution of diisobutylaluminum hydride in toluene ($\sim$12 mmole), dropwise over a period of 5 minutes. After 4 hours at $-78°$ C., excess of hydride was destroyed by dropwise addition of 1 ml of glacial acetic acid. The cooling bath was removed and 20 g of silica gel was added to the reaction mixture with stirring, followed by 1.5 ml of water dropwise. Stirring was continued for 30 minutes, whereupon the reaction mixture was filtered and the residual silica gel was washed successively with THF, 5% acetonitrile in ethyl acetate and finally with acetone. The combined filtrate was concentrated under reduced pressure and the crude residue was chromatographed on a silica gel column. Elution with 50% ethyl acetate in hexane, followed by ethyl acetate afforded 1.16 g of title epoxyaldehyde which crystallized on standing at $-20°$ C.

A(10) [1α,2β(5Z),3β,4α,5α,6α]-7-[5,6-Epoxy-3-(tetrahydropyranyloxymethyl)-7-oxabicyclo[2.2.1]hept-2-yl]-5-heptenoic acid, methyl ester A suspension of 5.77 g of freshly dried carboxybutyl-triphenylphosphonium bromide (13.03 mmol), in 50 ml of freshly distilled THF, cooled in an ice-water bath was treated dropwise with 12 ml of a 1.5M solution of K-t-amylate in toluene (19.2 mmole). The yellow-orange suspension was stirred at 0° C. for 30 minutes and finally at room temperature for 1 hour, whereupon it was cooled to $-20°$ C. and a solution of 2.33 g of Part A(9) epoxy aldehyde (8.69 mmole) in 10 ml of dry THF was added dropwise over a period of several minutes. An instant discolorization of the ylide solution was observed. The reaction mixture was stirred at $-20°$ C. for 2 hours, whereupon it was warmed to 0° C. and left for 15 minutes, prior to addition of glacial acetic acid. The reaction mixture was now diluted with ether and washed with water. The ether extract was washed several times with saturated sodium bicarbonate solution. The combined aqueous extract was now washed with ether (X2). The aqueous layer was now carefully acidified with 1N aqueous hydrochloric acid to pH 2. It was now extracted with ether and then with methylene chloride. The combined ether and methylene chloride extract was dried over anhydrous magnesium sulfate and concentated under reduced pressure. The crude residue was diluted with 75 ml of ether, cooled in an ice-water bath and an etheral diazomethane solution was added dropwise until the color persisted. After 30 minutes, excess diazomethane was removed by bubbling argon through the reaction mixture. It was now concentrated and the crude residue was chromatographed on a silica gel column. Elution with 15–40% ethyl acetate in hexane afforded 1.27 g of title 5Z-ester (contaminated with 10–15% of undesired 5E ester).

A(11) [1α,2β(5Z),3β,4α,5α,6α]-7-[5,6-Epoxy-3-hydroxymethyl-7-oxabicyclo-[2.2.1]hept-2-yl]-5-heptenoic acid, methyl ester To a solution of 1.27 g of Part A(10) tetrahydropyranyl ether (3.46 mmole) in 30 ml of methanol was added with stirring 250 mg of powdered and dried Amberlyst-15. After 6 hours at room temperature, the reaction mixture was diluted with ether and anhydrous magnesium sulfate was added. It was now filtered and the residual solid was washed thoroughly with ether. The combined organic extract was dried over anhydrous magnesium sulfate and concentrated under reduced pressure. The crude residue was chromatographed on a silica gel column and eluted with 50–75% ethyl acetate in hexane to obtain 892 mg of title alcohol ester.

B. N-Hexanoylglycine

Glycine (7.5 g, 100 mmol) was dissolved in NaOH solution (NaOH:8 g, H$_2$O:50 ml) and cooled to 0° C. Et$_2$O (50 ml) was added and n-hexanoyl chloride (13.4 g, 100 mmol) was then added dropwise over 60 minutes at 0° C. under vigorous stirring. The reaction was allowed to warm to room temperature and was stirred for 1 hour. 1N-NaOH (10 ml) was added and the layers were separated. The water layer was washed with Et$_2$O (20 ml×2). The combined Et$_2$O layers were extracted with 1N-NaOH (20 ml). The combined water layers were acidified with concentrated HCl to pH 2 and the products were extracted with Et$_2$O (100 ml×3). The combined Et$_2$O layers were washed with brine (50 ml) and dried over MgSO$_4$. Filtration and evaporation of solvent gave a colorless solid (16.2 g), which was crystallized from EtOAc (60 ml) to give colorless needle crystals (10.9 g, 63 mmol, 63%), m.p. 93°–96°. TLC: silica gel, MeOH, CH$_2$Cl$_2$, HCOOH; 10, 89.5, 0.5, PMA R$_f$=0.45.

C. [1α,2β(5Z),3β,4α,5α,6α]-7-[5,6-Epoxy-3-(tosyloxymethyl)-7-oxabicyclo[2.2.1]hept-2-yl]-5-heptenoic acid, methyl ester Tosyl chloride (4.256 g, 22.4 mmol) dissolved in CH$_2$Cl$_2$ (30 ml) is added dropwise to a magnetically stirred solution of [1α,2β(5Z),3β,4α,5α,6α]-7-[5,6-epoxy-3-(hydroxymethyl)-7-oxabicyclo[2.2.1]hept-2-yl]-5-heptenoic acid, methyl ester (prepared as described in Part A) (11.2 mmol) in pyridine (30 ml) at 0° C. After completion of the addition, the reaction is warmed to room temperature and stirred overnight. The reaction is poured into ice/H$_2$O and stirred for 30 minutes. The products are extracted with EtOAc (80 ml×3). The combined EtOAc layers are washed with 3N-HCl (40 ml×3), saturated NaHCO$_3$, brine and dried over MgSO$_4$. Filtration and evaporation of solvent gave a white solid, which is crystallized from isopropyl ether to give the corresponding title tosylate.

D. [1α,2β(5Z),3β,4α,5α,6α]-7-[5,6-Epoxy-3-(aminomethyl)-7-oxabicyclo[2.2.1]-hept-2-yl]-5-heptenoic acid, methyl ester The title B tosylate is subjected to a Gabriel synthesis to form the corresponding amino compound as described below.

The potassium phthalimide used is purified prior to use by boiling 5 g thereof with 9 ml acetone for 15 minutes, filtering while hot and washing with 5 ml acetone. The remaining solid is dried in vacuo for 6 hours at 100° C. prior to use.

The title B tosylate (19.2 mmol) and purified potassium phthalimide (6.4 g, 34.6 mmol, 1.8 equiv.) in dimethylsulfoxide (70 ml, Burdick & Jackson) are heated at 90°–100° C. for 2½ hours (checked by TLC Et$_2$O-pet ether 2:1, no tosylate remaining). After cooling to room temperature, water (90 ml) is added. The mixture is poured into ice water (~350 ml) and stirred 30 minutes. A solid is harvested by filtration and washed with more water. The solid is dissolved in warm ethyl acetate (150 ml), washed with water (3×50 ml), dried (MgSO$_4$), filtered and freed of solvent in vacuo. The remaining solid is recrystallized from isopropyl ether (~150 ml) to give corresponding phthalimide.

The above phthalimide is dissolved in distilled CH$_2$Cl$_2$ (24 ml) and distilled ethanol (104 ml) in an argon atmosphere. Anhydrous hydrazine (0.78 ml, 25.6 mmol) is added. The mixture is stirred at room temperature. After 8 hours an additional 0.2 ml of hydrazine is added and the mixture is stirred an additional 15 hours at room temperature. A white solid is removed by filtration and washed with more CH$_2$Cl$_2$. The filtrate is taken to dryness in vacuo (on the pump at end). Cold 0.5N HCl solution (80 ml) is added. A small amount of white solid is removed by filtration and washed with additional 0.5N HCl solution (80 ml). The acidic solution is washed with ether (2×100 ml) and then basified with solid K$_2$CO$_3$. The amine is extracted into CHCl$_3$ (3×100 ml), dried (MgSO$_4$) and freed of solvent in vacuo leaving an oil. Ether (100 ml) is added to this oil and after cooling in an ice bath, a solid is removed by filtration. The solvent is removed from the filtrate in vacuo leaving title amine. The material is used without further purification.

E. [1α,2β(5Z),3β,4α,5α,6α]-7-[5,6-Epoxy-3-[[[[(1-oxohexyl)amino]acetyl]amino]methyl]-7-oxabicyclo[2.2.1]hept-2-yl]-5-heptenoic acid, methyl ester Part B compound (260 mg, 1.5 mmol) is dissolved in distilled THF (12 ml) in an argon atmosphere. After cooling in an ice bath carbonyldiimidazole (CDI) (243 mg, 1.5 mmol) is added. The mixture is stirred cold for 1 hour and then at room temperature for 1 hour. The solution is cooled to 0° C. and a solution of Part D amine (1.5 mmol) in THF (3 ml) is added. The mixture is left stirring overnight at room temperature. The solvent is removed in vacuo and the residue is dissolved in CHCl$_3$ (50 ml). This is washed with 1N HCl (20 ml), 1N NaOH (20 ml) and H$_2$O (20 ml), dried (MgSO$_4$) and freed of solvent in vacuo leaving an oil. The oil is chromatographed on silica gel to give title compound.

EXAMPLE 2

[1α,2β(5Z),3β,4α,5α,6α]-7-[5,6-Epoxy-3-[[[[(1-oxohexyl)amino]acetyl]amino]methyl]-7-oxabicyclo[2.2.1]hept-2-yl]-5-heptenoic acid To a solution of 76 mg of Example 1 ester in 1 ml of THF is added with stirring 500 ml of a 1N aqueous lithium hydroxide solution. After stirring at room temperature for several hours, the reaction mixture is acidified with aqueous oxalic acid solution and extracted with methylene chloride. The methylene chloride extract is dried over anhydrous magnesium sulfate and concentrated. The crude residue is chromatographed on a silica gel column and eluted with 5–10% methanol in methylene chloride to obtain the title acid.

EXAMPLE 3

[1α,2β(5Z),3β,4α,5α,6α]-7-[5,6-Epoxy-3-[[[[[(butylamino)carbonyl]amino]acetyl]amino]methyl]-7-oxabicyclo[2.2.1]hept-2-yl]-5-heptenoic acid, methyl ester A. N-[(Butylamino)carbonyl]glycine, ethyl ester Glycine ethyl ester•HCl (5.58 g, 40 mmol) was suspended in distilled CH$_2$Cl$_2$ (20 ml). After cooling in an ice bath, distilled Et$_3$N (6.13 ml, 44 mmol) was added. Distilled n-butyl isocyanate (4.95 ml, 44 mmol) was added. The cooling bath was removed and the mixture was left stirring overnight at room temperature. Additional Et$_3$N (3.05 ml) was added and the mixture was stirred 3 more hours. After diluting with more CH$_2$Cl$_2$, the solution was washed with water (50 ml), 1N HCl (50 ml), saturated NaHCO$_3$ solution (50 ml) and water (50 ml). After drying (MgSO$_4$), the solvent was removed in vacuo leaving the title compound (7.641 g, 94%) which slowly crystallized. This was used without further purification.

B. N-[(Butylamino)carbonyl]glycine

Part A ethyl ester (3.378 g, 16.7 mmol) was dissolved in distilled THF (100 ml) and treated with 1N LiOH solution (40 ml). After stirring overnight at room temperature and acidifying with concentrated HCl, solid KCl was added. The layers were separated. The aqueous layer was reextracted with EtOAc (3×50 ml). The combined organic layers (THF and EtOAc) were washed with saturated NaCl solution (25 ml), dried (MgSO$_4$), and freed of solvent in vacuo leaving the title compound, as a white solid (2.81 g, 97%).

C. [1α,2β(5Z),3β,4α,5α,6α]-7-[5,6-Epoxy-3-[[[[[(butylamino)carbonyl]amino]acetyl]amino]methyl]-7-oxabicyclo[2.2.1]hept-2-yl]-5-heptenoic acid, methyl ester Part B compound (174.2 mg, 1 mmol) is partially dissolved in distilled THF (8 ml) in an argon atmosphere. After cooling in an ice bath, carbonyl diimidazole (CDI) (162 mg, 1 mmol) is added. The mixture is stirred cold 1 hour and at room temperature 1½ hours. The solution is cooled in an ice bath and a solution of chiral amine prepared in Example 1 Part D (1 mmol) in THF (3 ml) is added. The cooling bath is removed and the mixture is left stirring overnight at room temperature. The solvent is removed in vacuo. CHCl₃ (35 ml) is added to the residue. The solution is washed with 1N HCl (15 ml), 1N NaOH (15 ml) and H₂O (15 ml), dried (MgSO₄) and freed of solvent in vacuo leaving an oil. This is chromatographed on silica gel to give the title compound.

EXAMPLE 4

[1α,2β(5Z),3β,4α,5α,6α]-7-[5,6-Epoxy-3-[[[[[(butylamino)carbonyl]amino]acetyl]amino]methyl]-7-oxabicyclo[2.2.1]hept-2-yl]-5-heptenoic acid Example 3 methyl ester is hydroxyzed as described in Example 2 to form the title acid.

EXAMPLE 5

[1α,2β(5Z),3β,4α,5α,6α]-7-[5,6-Epoxy-3-[[[[(butoxycarbonyl)amino]acetyl]amino]methyl]-7-oxabicyclo[2.2.1]hept-2-yl]-5-heptenoic acid, methyl ester A. N-(Butoxycarbonyl)glycine ethyl ester Glycine ethyl ester•HCl (3.5 g, 25 mmol) was suspended in distilled CH₂Cl₂ (25 ml) in an argon atmosphere. After cooling to −40° C. distilled Et₃N (7.65 ml, 55 mmol) was added followed by dropwise addition of a solution of distilled n-butyl chloroformate (3.2 ml, ~25 mmol) in CH₂Cl₂ (10 ml). After stirring at −40° for 1 hour the mixture was left in a freezer (−5° C.) overnight. The mixture was stirred at −5° to −10° for 1 hour. More CH₂Cl₂ was added followed by water (50 ml). The layers were separated. The organic layer was washed with 1N HCl (50 ml), saturated NaHCO₃ solution (50 ml) and water (50 ml), dried (MgSO₄), and freed of solvent in vacuo leaving 3.129 g of material. This was combined with material from a 5 mmol run and chromatographed on silica gel (100 g, Baker for flash chromatography), eluting with ether-hexane 1:1 to give the title compound as an oil (3.196 g, 52.5%). TLC: silica gel, Et₂O-hexane 1:1, PMA, $R_f$=0.34.

B. N-(Butoxycarbonyl)glycine

The ethyl ester prepared in part A (3.141 g, 15.47 mmol) was dissolved in 100 ml distilled THF and treated with 1N LiOH solution (40 ml). The mixture was left stirring overnight at room temperature. After acidification with concentrated HCl and addition of solid KCl, the layers were separated. The aqueous layer was reextracted with EtOAc (3×50 ml). The combined organic layers (THF+EtOAc) were washed with saturated NaCl solution (25 ml), dried (MgSO₄) and freed of solvent in vacuo leaving the title compound (2.78 g, quant.) which slowly crystallized.

C. [1α,2β(5Z),3β,4α,5α,6α]-7-[5,6-Epoxy-3-[[[[(butoxycarbonyl)amino]acetyl]amino]methyl]-7-oxabicyclo[2.2.1]hept-2-yl]-5-heptenoic acid, methyl ester The acid prepared in part B (175.2 mg, 1 mmol) is dissolved in distilled THF (8 ml) in an argon atmosphere. After cooling in an ice bath carbonyldiimidazole (CDI) (1 mmol) is added. The mixture is stirred cold 1 hour and at room temperature 1 hour. The mixture is again cooled in an ice bath and a solution of chiral amine (prepared in Example 1 part D, (1 mmol) in THF (3 ml) is added. The cooling bath is removed and the mixture is left stirring overnight at room temperature. The solvent is removed in vacuo. CHCl₃ (35 ml) is added. The solution is washed with 1N HCl (15 ml), 1N NaOH (15 ml) and H₂O (15 ml), dried (MgSO₄) and freed of solvent in vacuo. The remaining oil is chromatographed on silica gel to give title compound.

EXAMPLE 6

[1α,2β(5Z),3β,4α,5α,6α]-7-[5,6-Epoxy-3-[[[[(butoxycarbonyl)amino]acetyl]amino]methyl]-7-oxabicyclo[2.2.1]hept-2-yl]-5-heptenoic acid The methyl ester prepared in Example 5 (0.396 mmol) is dissolved in distilled THF (16 ml) and water (3.8 ml) in an argon atmosphere and 1N LiOH solution (3.9 ml) is added. The mixture is stirred at room temperature 5½ hours, then neutralized with 1N HCl solution (3.8 ml). After adding solid KCl the layers are separated. The aqueous layer is reextracted with CHCl₃ (3×25 ml). The combined organic layers (THF+CHCl₃) are washed with saturated NaCl solution (15 ml), dried (MgSO₄) and freed of solvent in vacuo leaving an oil. This is chromatographed on silica gel and triturated with Et₂O to give the title compound.

EXAMPLE 7

[1α,2β(5Z),3β,4α,5α,6α]-7-[5,6-Epoxy-3-[[[1-oxo-2-[(1-oxohexyl)amino]propyl]amino]methyl]-7-oxabicyclo[2.2.1]hept-2-yl]-5-heptenoic acid, methyl ester A. (2R)-2-(Hexanoylamino)propionic acid D-alanine (20 mmol) and hexanoyl chloride (22 mmol) were reacted using the method as described in Example 1 Part B to give the title compound as a white crystalline material (2.45 g, 65.5%) after recrystallization from isopropyl ether (20 ml), m.p. 82°–95° C.

B. [1α,2β(5Z),3β,4α,5α,6α]-7-[5,6-Epoxy-3-[[[1-oxo-2-[(1-oxohexyl)amino]propyl]amino]methyl]-7-oxabicyclo[2.2.1]hept-2-yl]-5-heptenoic acid, methyl ester Part A acid compound (1 mmol) and chiral amine prepared as described in Example 1 Part D (1 mmol) are coupled using CDI (1 mmol) as described in Example 1 Part E. The crude product is chromatographed on silica gel and the eluted product is triturated with Et₂O to give the title methyl ester.

EXAMPLE 8

[1α,2β(5Z),3β,4α,5α,6α]-7-[5,6-Epoxy-3-[[[1-oxo-2-[(1-oxohexyl)amino]propyl]amino]methyl]-7-oxabicyclo[2.2.1]hept-2-yl]-5-heptenoic acid The Example 7 methyl ester (0.49 mmol) is hydrolyzed with LiOH solution in a THF-water mixture as described in Example 6. The viscous product is dissolved in EtOAc (~2–3 ml). On standing crystalline material is deposited. This is harvested by filtration and washed with Et₂O to give title acid.

EXAMPLE 9

[1α,2β(5Z),3β,4α,5α,6α]-7-[5,6-Epoxy-3-[[[2-methyl-2-[(1-oxohexyl)amino]-1-oxopropyl]amino]methyl]-7-oxabicyclo[2.2.1]hept-2-yl]-5-heptenoic acid, methyl ester A. 2-(Hexanoylamino)-2-methylpropionic acid 2-Aminoisobutyric acid (2.0 g, 19.4 mmol) and n-hexanoyl chloride (3.0 g, 22.4 mmol) were reacted in the presence of NaOH (1.6 g, 40 mmol) in a mixture of ether and water using the method described in Example 5, Part A. The title compound (1.90 g, 49%) was obtained after crystallization from benzene, m.p. 141°–143° C.

B. [1α,2β(5Z),3β,4α,5α,6α]-7-[5,6-Epoxy-3-[[[2-methyl-2-[(1-oxohexyl)amino]-1-oxopropyl]amino]methyl]-7-oxabicyclo[2.2.1]hept-2-yl]-5-heptenoic acid, methyl ester Part A compound (1 mmol) is reacted with CDI (1 mmol) and then with chiral amine prepared as described in Example 1 Part D (1 mmol) employing the method described in Example 1 Part E. The crude product is chromatographed on silica gel to give title ester.

EXAMPLE 10

[1α,2β(5Z),3β,4α,5α,6α]-7-[5,6-Epoxy-3-[[[2-methyl-2-[(1-oxohexyl)amino]-1-oxopropyl]amino]methyl]-7-oxabicyclo[2.2.1]hept-2-yl]-5-heptenoic acid The Example 10 methyl ester (0.51 mmol) is hydrolyzed with LiOH in a water-THF mixture as described in Example 6. The product is crystallized to give title acid.

EXAMPLE 11

[1α,2β(5Z),3β,4α,5α,6α]-7-[5,6-Epoxy-3-[[[[(4-phenylbenzoyl)amino]acetyl]amino]methyl]-7-oxabicyclo[2.2.1]hept-2-yl]-5-heptenoic acid, methyl ester A. 2-[(4-Phenylbenzoyl)amino]acetic acid Glycine (5 mmol) was reacted with 4-biphenylcarbonyl chloride (about 5 mmol) in the presence of 1N NaOH solution (10 ml), ether (21 ml) and THF (2 ml) using the procedure described in Example 5. Most of the product precipitated as a solid on acidification of the aqueous layer during the work up. This was found to be quite insoluble in CHCl₃ and EtOAc. It was largely dissolved in CH₃CN (~35 ml) and filtered to remove insoluble material. Crystalline acid (0.81 g, 63%) was deposited on cooling, m.p. 207°–218° C. decomp.

B. [1α,2β(5Z),3β,4α,5α,6α]-7-[5,6-Epoxy-3-[[[[(4phenylbenzoyl)amino]acetyl]amino]methyl]-7-oxabicyclo[2.2.1]hept-2-yl]-5-heptenoic acid, methyl ester Part A acid (1 mmol) is reacted with carbonyldiimidazole (1 mmole) followed by [1α,2β(5Z),3β,4α,5α,6α]-7-[5,6-epoxy-3-(amino-methyl)-7-oxabicyclo[2.2.1]hept-2-yl]-5-heptenoic acid, methyl ester (1 mmole) as in Example 1, Part E. After stirring overnight at room temperature. DMF is added and the mixture is left stirring an additional 24 hours. After the usual work up, the product is chromatographed on silica gel to give title ester.

EXAMPLE 12

[1α,2β(5Z),3β,4α,5α,6α]-7-5,6-Epoxy-3-[[[[(4-phenylbenzoyl)amino]acetyl]amino]methyl]-7-oxabicyclo[2.2.1]hept-2-yl]-5-heptenoic acid The Example 11 methyl ester (0.279 mmol) is hydrolyzed with LiOH as described in Example 6 to give a solid. This is triturated with EtOAc to give title acid.

EXAMPLE 13

[1α,2β(5Z),3β,4α,5α,6α]-7-[5,6-Epoxy-3-[[[[(1-oxopropyl)amino]acetyl]amino]methyl]-7-oxabicyclo[2.2.1]hept-2-yl]-5-heptenoic acid Following the procedure of Examples 1 and 2 except substituting propanoyl chloride for hexanoyl chloride, the title compound is obtained.

EXAMPLE 14

[1α,2β(5Z),3β,4α,5α,6α]-7-[5,6-Epoxy-3-[[[[(1-oxoethyl)amino]acetyl]amino]methyl]-7-oxabicyclo[2.2.1]hept-2-yl]-5-heptenoic acid Following the procedure of Examples 1 and 2 except substituting acetyl chloride for 6-hexanoyl chloride, the title compound is obtained.

EXAMPLE 15

[1α,2β(5Z),3β,4α,5α,6α]-7-[5,6-Epoxy-3-[[[[(1-oxo-2-butenyl)amino]acetyl]amino]methyl]-7-oxabicyclo[2.2.1]hept-2-yl]-5-heptenoic acid Following the procedure of Examples 1 and 2 except substituting 2-butenoyl chloride for hexanoyl chloride, the title compound is obtained.

EXAMPLE 16

[1α,2β(5Z),3β,4α,5α,6α]-7-[5,6-Epoxy-3-[[[[(1-oxo-3-butynyl)amino]acetyl]amino]methyl]-7-oxabicyclo[2.2.1]hept-2-yl]-5-heptenoic acid Following the procedure of Examples 1 and 2 except substituting 3-butynoyl chloride for hexanoyl chloride, the title compound is obtained.

EXAMPLE 17

[1α,2β(5Z),3β,4α,5α,6α]-7-[5,6-Epoxy-3-[[[[(phenylcarbonyl)amino]acetyl]amino]methyl]-7-oxabicyclo[2.2.1]hept-2-yl]-5-heptenoic acid Following the procedure of Examples 1 and 2 except substituting benzoyl chloride for hexanoyl chloride, the title compound is obtained.

EXAMPLE 18

[1α,2β,3β,4α,5α,6α)-7-[5,6-Epoxy-3-[[[[(1-oxohexyl)amino]acetyl]amino]methyl]-7-oxabicyclo[2.2.1]hept-2-yl]heptanoic acid A. (1α,2β,3β,4α,5α,6α)-7-[3-(Hydroxymethyl)-7-oxabicyclo[2.2.1]hept-2-yl]heptanoic acid, methyl ester To 800 mg (3.0 mmole) of the (1α,2β,3β,4α, 5α,6α)-7-[3-(hydroxymethyl)-7-oxabicyclo[2.2.1]hept-2-yl]-5-heptenoic acid, methyl ester dissolved in 120 ml of ethyl acetate is added, under an argon atmosphere, 160 mg of 5% Pd on carbon. The argon atmosphere is exchanged for a slight positive pressure of hydrogen and the reaction is stirred for 8 hours at 25°, filtered through a celite plug and evaporated to provide the title A compound.

B. (1α,2β,3β,4α,5α,6α)-7-[5,6-Epoxy-3-[[[[(1-oxohexyl)amino]acetyl]amino]methyl]-7-oxabicyclo[2.2.1]hept-2-yl]heptanoic acid Following the procedure of Examples 1 and 2 except substituting the Part A alcohol-ester for the alcohol ester employed in Example 1 Part C, the title product is obtained.

EXAMPLE 19

(1α,2β,3β,4α,5α,6α)-7-[5,6-Epoxy-3-[[[[(1-oxobutyl)amino]acetyl]amino]methyl]-7-oxabicyclo[2.2.1]hept-2-yl]heptanoic acid Following the procedure of Example 18 except substituting butanoyl chloride for hexanoyl chloride, the title compound is obtained.

EXAMPLE 20

(1α,2β,3β,4α,5α,6α)-7-[5,6-Epoxy-3-[[[[(1-oxo-2-propenyl)amino]acetyl]amino]methyl]-7-oxabicyclo[2.2.1]hept-2-yl]heptanoic acid Following the procedure of Example 18 except substituting propenyl chloride for hexanoyl chloride, the title compound is obtained.

EXAMPLE 20

[1α,2β(Z),3β,4α,5α,6α]-6-[5,6-Epxoy-3-[[[[(1-oxohexyl)amino]acetyl]amino]methyl]-7-oxabicyclo[2.2.1]hept-2-yl]-1-(1H-tetrazol-5-yl)-4-hexene A. [1α,2β(Z),3β,4α,5α,6α]-6-[5,6-Epoxy-3-hydroxymethyl-7-oxabicyclo[2.2.1]-hept-2-yl]-1-(1H-tetrazol-5-yl)-4-hexene To 5.5 g (11.8 mmole) of triphenyl-4-(1H-tetrazol-5-yl)butyl phosphonium bromide in 100 ml of tetrahydrofuran (THF) at 0° is added 2.78 g (23.6 mmole) potassium t-butoxide. The reaction is stirred at 25° for 30 minutes and [1α,2β,4α,5α,6α]-[[5,6-epoxy-2-hydroxymethyl]-7-oxabicyclo[2.2.1]heptyl]-3-acetaldehyde (prepared by aqueous acid treatment of tetrahydropyranyloxy ether L) (2 g, 11.8 mmole) is added in 30 ml of THF. The reaction is stirred for 2 hours and quenched with dilute aqueous HCl. The aqueous layer is extracted with 250 ml of ethyl acetate. The combined organic solutions are evaporated in vacuo, diluted with 500 ml of a 5% NaHCO$_3$ solution, washed with 100 ml of ether, acidified with dilute HCl to pH 3, and extracted with three 500 ml portions of ethyl acetate. The combined organic solutions are dried over anhydrous MgSO$_4$, and purified by silica chromatography using a 5% methanol in methylene chloride eluant to provide title A compound.

B. [1α,2β(5Z),3β,4α,5α,6α]-6-[5,6-Epoxy-3-[[[[(1oxohexyl)amino]acetyl]amino]methyl]-7-oxabicyclo[2.2.1]hept-2-yl]-1-(1H-tetrazol-5-yl)-4-hexene Following the procedure of Examples 1 and 2 except substituting the Part A compound for the hydroxymethyl compound used in Example 1 Part C, the title compound is obtained.

EXAMPLE 21

[1α,2β(5Z),3β,4α,5α,6α]-7-[5,6-Epoxy-3-[[[[(1-oxo-4-phenyl)butyl]amino]acetyl]amino]methyl]-7-oxabicyclo[2.2.1]hept-2-yl]-5-heptenoic acid A. 4-Phenylbutanoyl glycine ethyl ester 4-Phenylbutyric acid (2.46 g, 15 mmol) was dissolved in distilled THF (70 ml) in an argon atmosphere. After cooling in an ice bath, carbonyldiimidazole (CDI) (2.43 g, 1.5 mmol) was added and the mixture was stirred cold 1 hour and at room temperature 1 hour. The mixture was then cooled and glycine ethyl ester•HCl (2.09 g, 15 mmol) and distilled Et$_3$N (2.1 ml, 15 mmol) were added. The mixture was left stirring overnight at room temperature. After removal of the solvent in vacuo, Et$_2$O (200 ml) was added. The solution was washed with 1N HCl (70 ml), 0.5N NaOH (70 ml) and saturated NaCl solution (70 ml), dried (MgSO$_4$) and freed of solvent in vacuo leaving title compound (3.13 g, 84%) as white crystalline material. TLC: silica gel, Et$_2$O, UV; R$_f$: 0.58.

B. 4-Phenylbutanoyl glycine

The Part A ester (3.07 g, 12.3 mmol) was hydrolyzed with NaOH (5 g, 125 mmol) in water (60 ml). After stirring at room temperature 6 hours, neutral material was removed by washing with Et$_2$O (2×50 ml). The aqueous solution was then acidified with concentrated HCl solution. The product was extracted into CHCl$_3$ (3×60 ml), dried (MgSO$_4$) and freed of solvent in vacuo leaving a white solid. This was recrystallized from EtOAc (10 ml) to give title compound (2.18 g, 80%), m.p. 99°-101° C.

C. [1α,2β(5Z),3β,4α,5α,6α]-7-[5,6-Epoxy-3-[[[[(1-oxo-4-phenyl)butyl]amino]acetyl]amino]methyl]-7-oxabicyclo-[2.2.1]hept-2-yl]-5-heptenoic acid, methyl ester Part B acid (1 mmol) is reacted with CDI (1 mmol) and then with Example 1 Part D chiral amine (1 mmol) as described in Example 1 Part E. The crude product is chromatographed on silica gel to give title compound.

D. [1α,2β(5Z),3β,4α,5α,6α]-7-[5,6-Epoxy-3-[[[[(1-oxo-4-phenyl)butyl]amino]acetyl]amino]methyl]-7-oxabicyclo-[2.2.1]hept-2-yl]-5-heptenoic acid The Part C methyl ester (0.71 mmol) is hydrolyzed with LiOH in a water-THF mixture as described in Example 6 The crude crystalline product is recrystallized to give title compound.

EXAMPLE 22

[1α,2β(Z),3β,4α,5α,6α]-7-[5,6-Epoxy-3-[[[[[(phenylthio)acetyl]amino]acetyl]amino]methyl]-7-oxabicyclo[2.2.1]hept-2-yl]-5-heptenoic acid A. (Phenylthio)acetyl glycine ethyl ester The title ethyl ester was prepared from thiophenoxy acetic acid (15 mmol) and the ethyl ester of glycine•HCl using carbonyldiimidazole (CDI) as described in Example 21, Part A giving 2.95 g (78%) of solid.

B. (Phenylthio)acetyl glycine

The Part A ethyl ester was hydrolyzed with aqueous NaOH as described in Example 21 Part B to give the title acid (1.041 g, 92%) as a crystalline material.

C. [1α,2β(Z),3β,4α,5α,6α]-7-[5,6-Epoxy-3-[[[[[(phenylthio)acetyl]amino]acetyl]amino]methyl]-7-oxobicyclo[2.2.1]hept-2-yl]-5-heptenoic acid, methyl ester The Part B acid (1.5 mmol) is reacted with CDI (1.5 mmol) followed by Example 1 Part D chiral amine (1.5 mmol) as described in Example 1 Part E. The crude product is chromatographed on silica gel to give title ester.

D. [1α,2β(Z),3β,4α,5α,6α]-7-[5,6-Epoxy-3-[[[[[(phenylthio)acetyl]amino]acetyl]amino]methyl]-7-oxabicyclo[2.2.1]hept-2-yl]-5-heptenoic acid The Part C methyl ester (0.98 mmol) is hydrolyzed with 1N LiOH (2 equivalents) as described in Example 6. The crude product is recrystallized to give title acid.

EXAMPLE 23

[1α,2β(Z),3β,4α,5α,6α]-7-[5,6-Epoxy-3-[[[[3-(4-hydroxyphenyl)-1-oxopropyl]amino]acetyl]amino]methyl]-7-oxabicyclo[2.2.1]hept-2-yl]-5-heptenoic acid A. 3-(4-Hydroxyphenyl)propanoyl glycine ethyl ester 3-(4-Hydroxyphenyl)propionic acid (2.49 g, 15 mmol) was reacted with glycine ethyl ester hydrochloride in the presence of CDI and Et$_3$N as described in Example 21 Part A. After removal of the solvent the residue was dissolved in CHCl$_3$ and washed with 1N HCl, saturated NaHCO$_3$ solution and saturated NaCl solution. After drying (MgSO$_4$) and removal of the solvent in vacuo crude title ester remained (2.44 g) as a viscous oil. NMR indicated this contained a major impurity but it was used without further purification.

B. 3-(4-Hydroxyphenyl)propanoyl glycine

Crude Part A ethyl ester was hydrolyzed with NaOH in water as described in Example 56 Part B to give a white solid (1.37 g). This was recrystallized from EtOAc•MeOH to give the title solid (0.98 g, 29% from starting acid).

C. [1α,2β(Z),3β,4α,5α,6α]-7-[5,6-Epoxy-3-[[[[3-(4-hydroxyphenyl)-1-oxopropyl]amino]acetyl]amino]methyl]-7-oxabicyclo[2.2.1]hept-2-yl]-5-heptenoic acid, methyl ester Example 1, Part D chiral amine (1.5 mmol) is dissolved in distilled THF (20 ml) in an argon atmosphere. Part B acid (346 mg, 1.55 mmol) is added and the mixture is cooled in an ice bath. Dicyclohexylcarbodiimide (DCC) (319 mg, 1.55 mmol) is added and the mixture is stirred cold 20 minutes and at room temperature overnight. 1N HCl (4 drops) is added and after stirring 10 minutes the solvent is removed in vacuo. EtOAc (8 ml) is added to the residue. After cooling in an ice bath the solid is removed by filtration and washed with cold EtOAc (~10 ml). The filtrate is freed of solvent in vacuo and the remaining material is chromatographed on silica gel to give title ester.

D. [1α,2β(Z),3β,4α,5α,6α]-7-[5,6-Epoxy-3-[[[[3-(4-hydroxyphenyl)-1-oxopropyl]amino]acetyl]amino]methyl]-7-oxabicyclo [2.2.1]hept-2-yl]-5-heptenoic acid The Part C methyl ester (0.51 mmol) is dissolved in distilled THF (20 ml) and water (2 ml) in an argon atmosphere and treated with 1N LiOH solution (3 ml). The reaction is complete in 1 hour and at 2 hours is worked up as described in Example 6 to form title product.

EXAMPLE 24

[1α,2β(Z),3β,4α,5α,6α]-7-[5,6-Epoxy-3-[[[[(phenoxyacetyl)amino]acetyl]amino]methyl]-7-oxabicyclo[2.2.1]hept-2-yl]-5-heptenoic acid A. Phenoxyacetyl glycine Glycine (20 mmol) was reacted with distilled phenoxyacetyl chloride (22 mmol) in the presence of NaOH (40 mmol) in a mixture of water and ether as described in Example 5 Part A. The crude product was recrystallized from EtOAc (15 ml) to give title acid (2.38 gm, 57%).

B. [1α,2β(Z),3β,4α,5α,6α]-7-[5,6-Epoxy-3- [[[[(phenoxyacetyl)amino]acetyl]amino]methyl]-7-oxabicyclo[2.2.1]hept-2-yl]-5-heptenoic acid, methyl ester Part A acid (1.5 mmol) is reacted with CDI (1.5 mmol), followed by Example 1 Part D chiral amine (1.5 mmol) as described in Example 1, Part E. The crude product is chromatographed on silica gel to give title ester.

C. [1α,2β(5Z),3β,4α,5α,6α]-7-[5,6-Epoxy-3-[[[[(phenoxyacetyl)amino]acetyl]amino]methyl]-7-oxabicyclo[2.2.1]hept-2-yl]-5-heptenoic acid The Part B methyl ester (1.01 mmol) is hydrolyzed with 1N LiOH (2 equivalents) in a THF-H₂O mixture as described in Example 6 to give a white solid. This is recrystallized to give title acid.

EXAMPLE 25

[1α,2β(5Z),3β,4α,5α,6α]-7-[5,6-Epoxy-3-[[[[(1-oxo-3-phenylpropyl)amino]acetyl]amino]methyl]-7-oxabicyclo[2.2.1]hept-2-yl]-5-heptenoic acid A. 3-Phenylpropanoyl glycine Glycine (1.5 g, 20 mmol) and hydrocinnamoyl chloride (3.37 g, 22 mmol) were reacted in the presence of NaOH (40 mmol) in a mixture of water and ether using the method described in Example 5 Part A. The crude product was extracted into chloroform, dried (MgSO₄) and freed of solvent in vacuo leaving a near white solid (3.53 g, 85%). This was recrystallized from EtOAc (13 ml) to give title compound (2.66 g, 64%) m.p. 112°-114° C.

B. [1α,2β(5Z),3β,4α,5α,6α]-7-[5,6-Epoxy-3-[[[[(1-oxo-3-phenylpropyl)amino]acetyl]amino]methyl]-7-oxabicyclo[2.2.1]hept-2-yl]-5-heptenoic acid, methyl ester Part A acid (1 mmol) is reacted with CDI (1 mmol) and then with Example 1 Part D chiral amine (1 mmol) as described in Example 1 Part E. The crude product is chromatographed on silica gel to give title compound.

C. [1α,2β(5Z),3β,4α,5α,6α]-7-5,6-Epoxy-3-[[[[(1-oxo-3-phenylpropyl)amino]acetyl]amino]methyl]-7-oxabicyclo[2.2.1]hept-2-yl]-5-heptenoic acid The Part B methyl ester (0.72 mmol) is hydrolyzed with LiOH in a water-THF mixture as described in Example 6. The crude crystalline product is recrystallized to give title compound.

EXAMPLE 26

[1α,2β(5Z),3β,4α,5α,6α]-7-[5,6-Epoxy-3-[[[[(1-oxo-5-phenylpentyl)amino]acetyl]amino]methyl]-7-oxabicyclo[2.2.1]hept-2-yl]-5-heptenoic acid A. 5-Phenylpentanoyl glycine ethyl ester 5-Phenylvaleric acid (2.67 g, 15 mmol) in distilled THF was reacted with CDI (15 mmol) followed by glycine ethyl ester•HCl (15 mmol) and (C₂H₅)₃N (15 mmol) as described in Example 56 Part A. The crude material (3.25 g, 82%) was used without purification.

B. 5-Phenylpentanoyl glycine

The Part A ester (12.34 mmol) was hydrolyzed with NaOH in water as described in Example 21 Part B. The crude product was recrystallized from EtOAc (12 ml) to give title compound (2.39 g, 82%), m.p. 93°-96° C.

C. [1α,2β(5Z),3β,4α,5α,6α]-7-5,6-Epoxy-3-[[[[(1-oxo-5-phenylpentyl)amino]acetyl]amino]methyl]-7-oxabicyclo[2.2.1]hept-2-yl]-5-heptenoic acid, methyl ester Part B compound (1 mmol) is reacted with CDI (1 mmol) and then with Example 1 Part D chiral amine (1 mmol) as described in Example 1 Part E. The crude product is chromatographed on silica gel to give title compound.

D. [1α,2β(5Z),3β,4α,5α,6α]-7-[5,6-Epoxy-3-[[[[(1-oxa-5-phenylpentyl)amino]acetyl]amino]methyl]-7-oxabicyclo[2.2.1]hept-2-yl]-5-heptenoic acid The Part C methyl ester (0.749 mmol) is hydrolyzed with LiOH in a water-THF mixture as described in Example 6. The crude crystalline product is recrystallized to give title compound.

EXAMPLE 27

[1α,2β(5Z),3β,4α,5α,6α]-7-[5,6-Epoxy-3-[[[[(4-cyclohexyl-1-oxobutyl)amino]acetyl]amino]methyl]-7-oxabicyclo2.2.1]hept-2-yl]-5-heptenoic acid A. 4-Cyclohexylbutanoic acid 4-Phenylbutanoic acid prepared as described in Example 21, Part A was dissolved in glacial acetic acid (25 ml). Platinum oxide (0.1 g) was added and the solution was hydrogenated in the Paar shaker at up to 55 p.s.i. until hydrogen uptake ceased (6.5 hours). The catalyst was removed by filtration and the acetic acid was removed in vacuo. The product crystallized and was recrystallized from Et$_2$O (20 ml) to give title compound (1.18 g, 77%), m.p. 85°–88° C.

B. [1α,2β(Z),3β,4α,5α,6α]-7-[5,6-Epoxy-3-[[[[(4-cyclohexyl-1-oxobutyl)amino]acetyl]amino]methyl]-7-oxabicyclo[2.2.1]hept-2-yl]-5-heptenoic acid, methyl ester The Part A acid (1.5 mmol) is dissolved in CHCl$_3$ (10 ml) in an argon atmosphere. The solution is cooled in an ice bath and carbonyldiimidazole (2.43 mg, 1.5 mmol) is added. The mixture is stirred cold 30 minutes and at room temperature 1 hour. The hydrochloride of the chiral amine (prepared as described in Example 1 Part D) (1.5 mmol) is added. The solution is cooled in an ice bath and tri-n-butylamine (0.36 ml, 278 mg, 1.5 mmol) is added and the mixture is left stirring overnight at room temperature. More CHCl$_3$ (40 ml) is added and the solution is washed with 1N HCl (20 ml), saturated NaHCO$_3$ solution (20 ml) and saturated NaCl solution (20 ml). After drying (MgSO$_4$), the solvent is removed in vacuo. The product is purified by chromatography on silica gel to give the title methyl ester.

C. [1α,2β(Z),3β,4α,5α,6α]-7-[5,6-Epoxy-3-[[[[(4-cyclohexyl-1-oxobutyl)amino]acetyl]amino]methyl]-7-oxabicyclo[2.2.1]hept-2-yl]-5-heptenoic acid The Part B methyl ester (1.39 mmol) is hydrolyzed with LiOH as described in Example 6. The crude crystalline product is recrystallized to give title acid compound.

EXAMPLE 28

[1α,2β(Z),3β,4α,5α,6α]-7-[5,6-Epoxy-3-[[[[1-oxo-3-(phenylthio)propyl]amino]acetyl]amino]methyl]-7-oxabicyclo[2.2.1]hept-2-yl]-5-heptenoic acid A. 3-(Phenylthio)propanoic acid, methyl ester Thiophenol (440 mg, 4 mmol) and Et$_3$N (70 μl, 0.5 mmol) were dissolved in CH$_2$Cl$_2$ (5 ml). Methyl acrylate (412 mg, 4.8 mmol) was added dropwise. The reaction was exothermic. After stirring at room temperature for 30 minutes, the excess methyl acrylate was removed in vacuo. TLC: silica gel, Et$_2$O-hexane 1:2, UV R$_f$=0.58. The crude title ester was used without further purification.

B. 3-(Phenylthio)propanoic acid

The crude Part A methyl ester (~4 mmole) was treated with 10 ml 1N NaOH and THF (5 ml). After stirring at room temperature 3 hours, ether (30 ml) was added. The layers were separated and the ether layer was reextracted with 1N NaOH solution (10 ml). The combined aqueous layers were washed with Et$_2$O (20 ml) and then acidified with concentrated HCl. The product was extracted with CHCl$_3$ (2×30 ml). The chloroform extracts were washed with saturated NaCl solution (2×20 ml), dried (MgSO$_4$) and freed of solvent in vacuo leaving title acid as a white solid (quant.). This was used without further purification.

C. 3-(Phenylthio)propanoyl glycine ethyl ester

Part B acid (0.740 g, 4.06 mmol) was reacted with carbonyldiimidazole (4.06 mmol) followed by glycine ethyl ester•HCl (4.06 mmol) as described in Example 56 Part A to give the title ester (1.00 g, 92%) as crystalline material.

D. 3-(Phenylthio)propanoyl glycine

The Part C ethyl ester (0.96 g, 3.6 mmol) was hydrolyzed with NaOH solution as described in Example 56 Part B to give a white solid which was triturated with Et$_2$O to give title acid (0.75 g, 87%).

E. [1α,2β(Z),3β,4α,5α,6α]-7-[5,6-Epoxy-3-[[[[[1-oxo-3-(phenylthio)propyl]amino]acetyl]amino]methyl]-7-oxabicyclo[2.2.1]hept-2-yl]-5-heptenoic acid, methyl ester The Part D acid (359 mg, 1.5 mmol) is reacted with carbonyldiimidazole (1.5 mmol) followed by the hydrochloride of Example 1 Part D chiral amine by the procedure described in Example 27 Part B. The crude product is chromatographed on silica gel to give title methyl ester.

F. [1α,2β(Z),3β,4α,5α,6α]-7-[5,6-Epoxy-3-[[[[[1-oxo-3-(phenylthio)propyl]amino]acetyl]amino]methyl]-7-oxabicyclo[2.2.1]hept-2-yl]-5-heptenoic acid The Part E methyl ester (1.285 mmol) is dissolved in THF (25 ml) and H$_2$O (2.5 ml) in an argon atmosphere and treated with 1N LiOH solution (2.6 ml). The mixture is stirred at room temperature for 5 hours and then worked up as described in Example 6. The crude product is chromatographed on silica gel to give title acid.

EXAMPLE 29

[1α,2β(Z),3β,4α,5α,6α]-7-[5,6-Epoxy-3-[[[[[(phenylmethyl)thio]acetyl]amino]acetyl]amino]methyl]-7-oxabicyclo[2.2.1]hept-2-yl]-5-heptenoic acid A. Chloroacetyl glycine Glycine (1.5 g, 20 mmol) was dissolved in 2N NaOH (25 ml, 50 mmol) and ether (20 ml) was added. Chloroacetyl chloride (2.26 g) dissolved in Et$_2$O (20 ml) was added dropwise at 0° C. The mixture was stirred at 0° for 30 minutes and at room temperature 1 hour. The layers were separated and the water layer was washed with Et$_2$O (2×20 ml). The water layer was then acidified to pH 2 with concentrated HCl and the product was extracted into EtOAc (3×50 ml). The combined EtOAc extracts were washed with brine, dried (MgSO$_4$), and freed of solvent in vacuo to give title acid compound as a solid (2.56 g, 84%) which was used without further purification.

B. (Benzylthio)acetyl glycine

Part A acid (1.28 g, 8.4 mmol) was dissolved in methanol (10 ml) and cooled in an ice bath. Sodium methoxide (1.08 g, 20 mmol) was added followed by dropwise addition of benzyl mercaptan (1.25 g, 10.08 mmoles). After stirring overnight at room temperature, 1N NaOH solution (10 ml) was added. Ether washes (2×40 ml) removed neutral material. The aqueous layer was then acidified to pH 2 with concentrated HCl. The product was extracted with Et$_2$O (3×50 ml), washed with brine, dried (MgSO$_4$) and freed of solvent in vacuo leaving a white solid. This was recrystallized from benzene to give title acid compound (1.28 g, 64%).

C. [1α,2β(Z),3β,4α,5α,6α]-7-[5,6-Epoxy-3-[[[[[[(phenylmethyl)thio]acetyl]amino]acetyl]amino]methyl]-7-oxabicyclo[2.2.1]hept-2-yl]-5-heptenoic acid, methyl ester Part B acid (1.5 mmol) is reacted with carbonyldiimidazole (1.5 mmol) followed by Example 1 Part D chiral amine•HCl 3 (1.5 mmol) using the procedure described in Example 27. The crude product is chromatographed on silica gel to give title ester.

D. [1α,2β(Z),3β,4α,5α,6α]-7-[5,6-Epoxy-3-[[[[[[(phenylmethyl)thio]acetyl]amino]acetyl]amino]methyl]-7-oxabicyclo[2.2.1]-hept-2-yl]-5-heptenoic acid The Part C methyl ester (1.28 mmol) is hydrolyzed with 1N LiOH solution (2.6 ml) in a THF-water mixture as described in Example 6. The reaction mixture is worked to form crude product which is recrystallized to give title product.

EXAMPLE 30

[1α,2β(Z),3β,4α,5α,6β]-7-[5,6-Epoxy-3-[[[[[(butyl-thio)acetyl]amino]acetyl]amino]methyl]-7-oxabicyclo[2.2.1]hept-2-yl]-5-heptenoic acid A. (Butanethio)acetyl glycine Example 29 Part A acid compound (1.28 g, 8.4 mmol) was reacted with 1-butanethiol using the procedure described in Example 29. The crude product was crystallized with diisopropylether (~10 ml) to give title acid (0.55 g, 32%).

B. [1α,2β(Z),3β,4α,5α,6α]-7-[5,6-Epoxy-3-[[[[[(butylthio)acetyl]amino]acetyl]amino]methyl]-7-oxabicyclo[2.2.1]hept-2-yl]-5-heptenoic acid, methyl ester Part A acid (1.5 mmol) is reacted with carbonyldiimidazole (1.5 mmol) followed by Example 1 Part D chiral amine hydrochloride (1.5 mmol) using the procedure described in Example 27. The crude product is chromatographed on silica gel to give title compound.

C. [1α,2β(Z),3β,4α,5α,6α]-7-[5,6-Epoxy-3-[[[[[(butylthio)acetyl]amino]acetyl]amino]methyl]-7-oxabicyclo[2.2.1]hept-2-yl]-5-heptenoic acid The Part B methyl ester (1.18 mmol) is hydrolyzed with 1N LiOH solution (2.4 ml) in a tetrahydrofuran-water mixture using the procedure described in Example 6. The reaction mixture is worked up in 5 hours. The crude product is crystallized from EtOAC (20 ml) to give title product.

EXAMPLE 31

[1α,2β(Z),3β,4α,5α,6α]-7-[5,6-Epoxy-3-[[[[[(Cyclohexylmethyl)thio]acetyl]amino]acetyl]amino]methyl]-7-oxabicyclo[2.2.1]hept-2-yl]-5-heptenoic acid A. Cyclohexylmethylthiol acetate Cyclohexylmethyl mesylate (1.92 g, 10 mol) and KSCOCH$_3$ (1.25 g) were suspended in distilled tetrahydrofuran (THF). The reaction mixture was heated under reflux for 3 hours. Additional KSCOCH$_3$ (1.25 g) and THF (9 ml) were added and the mixture was heated under reflux an additional 3 hours. Et$_2$O (100 ml) was added and the mixture was washed with brine (30 ml). The aqueous layer was reextracted with Et$_2$O (30 ml). The combined organic layers were washed with brine (15 ml), dried (MgSO$_4$) and freed of solvent to give a straw colored oil (1.8 g). This was chromatographed on silica gel (50 g, Baker for flash chromatography) eluting with 2% Et$_2$O in hexane to give title compound (1.189 g, 69%) as an oil. TLC: silica gel, 10% Et$_2$O in hexane, UV and I$_2$, R$_f$=0.48.

B. [(Cyclohexylmethyl)thio]acetyl glycine

Part A compound (6 mmol) and the Example 29 Part A acid (6 mmol) were reacted in the presence of NaOMe (17 mmol) as described in Example 29 Part B. The crude product was crystallized from diisopropyl ether to give title compound (516 mg, 35%).

C. [1α,2β(Z),3β,4α,5α,6α]-7-5,6-Epoxy-3-[[[[[(cyclohexylmethyl)thio]acetyl]amino]acetyl]amino]methyl]-7-oxabicyclo[2.2.1]hept-2-yl]-5-heptenoic acid, methyl ester Part B compound (1.5 mmol) is coupled with Example 1 Part D chiral amine•HCl (1.5 mmol) in the presence of carbonyl diimidazole (CDI) (1.5 mmol) as described in Example 27 Part B. The crude product is chromatographed on silica gel to give title compound.

D. [1α,2β(Z),3β,4α,5α,6α]-7-[5,6-Epoxy-3-[[[[[(cyclohexylmethyl)thio]acetyl]amino]acetyl]amino]methyl]-7-oxabicyclo[2.2.1]hept-2-yl]-5-heptenoic acid The Part C methyl ester (1.09 mmol) is hydrolyzed with 1N LiOH (4 ml) in a mixture of THF and water as described in Example 6. The crude product is recrystallized to give title acid.

EXAMPLE 32

[1α,2β(Z),3β,4α,5α,6α]-7-[5,6-Epoxy-3-[[[[ 8(phenylsulfinyl)acetyl]amino]acetyl]amino]methyl]-7-oxabicyclo[2.2.1]hept-2-yl]-5-heptenoic acid Powdered NaIO$_4$ (385 mg, 1.8 mmol) is dissolved in water (12 ml). A solution of Example 22 acid compound (0.6 mmol) in methanol (20 ml) is added. The mixture is stirred overnight at room temperature. Most of the methanol is removed in vacuo. Saturated NaCl solution (50 ml) is added. The product is extracted with CHCl$_3$ (3×50 ml). The combined chloroform extracts are washed with NaCl solution (20 ml), dried (MgSO$_4$), and freed of solvent in vacuo leaving an oil. This is chromatographed on silica gel to give title acid.

EXAMPLE 33

[1α,2β(Z),3β,4α,5α,6α]-7-[5,6-Epoxy-3-[[[[[(phenylsulfonyl)acetyl]amino]acetyl]amino]methyl]-7-oxabicyclo[2.2.1]hept-2-yl]-5-heptenoic acid Example 22 acid compound (0.9 mmol) is dissolved in methanol (10 ml) and cooled in an ice bath. Oxone (810 mg ~2.7 mmol) dissolved in water (10 ml) is added. The mixture is stirred at room temperature 4 hours, then diluted with water (30 ml). The product is extracted into CHCl$_3$ (3×35 ml). The combined CHCl$_3$ extracts are washed with saturated NaCl solution (2 x 20 ml), dried (MgSO$_4$), and freed of solvent in vacuo leaving an oil. This is chromatographed on silica gel to give title acid.

EXAMPLES 34 TO 69

Following the procedures outlined in the specification and described in the above working Examples, the following compounds may be prepared.

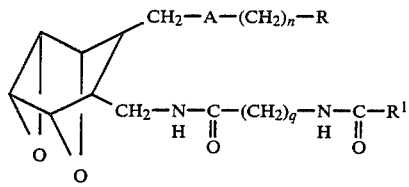

| Ex. No. | A | $(CH_2)_n$ | R | $(CH_2)_q$ | $R^1$ |
|---|---|---|---|---|---|
| 34. | CH=CH | $-CH(CH_3)-$ | $CO_2H$ | $(CH_2)_7$ | $-CH_2-CH=C(H)-CH_3-$ |
| 35. | $(CH_2)_2$ | $-C(CH_3)_2-$ | $CO_2H$ | $-CH(CH_3)-$ | $OC_6H_5$ |
| 36. | $(CH_2)_2$ | $(CH_2)_4$ | $CO_2H$ | $-CH_2-$ | $C_6H_5$ |
| 37. | CH=CH | $-C(CH_3)_2-CH_2-$ | $CO_2Li$ | $-CH_2-CH(CH_3)-$ | $CH_2C_6H_5$ |
| 38. | CH=CH | $-CH(CH_3)-CH(CH_3)-$ | $CO_2Na$ | $-CH_2-C(CH_3)_2-$ | $-(CH_2)_2C_6H_5$ |
| 39. | $(CH_2)_2$ | $-C(CH_3)(F)-CH_2-$ | $CO_2$glucamine salt | $-CH_2-CH(CH_3)-CH_2-$ | $-C_6H_4-p-CH_3$ |
| 40. | CH=CH | $-CH(F)-CH(F)-$ | $CO_2$tris salt | $-(CH_2)_3-$ | $-C_6H_4-p-OH$ |
| 41. | $(CH_2)_2$ | $-C(F)_2-CH_2-$ | $CO_2H$ | $-CH_2-CH(C_2H_5)-$ | $-OCH_2C_6H_5$ |
| 42. | $(CH_2)_2$ | $-(CH_2)_5-$ | tetrazolyl (N-H) | $-CH_2-CH(CH_3)-CH_2-$ | $-SC_2H_5$ |
| 43 | CH=CH | $-CH_2-CH(CH_3)-CH_2-$ | $CO_2H$ | $-C(CH_3)_2-CH_2-$ | $-OC_6H_5$ |
| 44. | $(CH_2)_2$ | $-CH_2-C(CH_3)_2-$ | $CO_2H$ | $(CH_2)_2$ | $C_3H_7$ |
| 45. | CH=CH | $CH_2$ | $CO_2H$ | $-CH_2-$ | $-NHCH_3$ |
| 46. | $(CH_2)_2$ | $(CH_2)_2$ | $CO_2H$ | $-CH_2-C(CH_3)_2-$ | $-NHC_6H_5$ |
| 47. | CH=CH | $(CH_2)_3$ | $CO_2H$ | $-CH_2-CH(CH_3)-CH(CH_3)-CH_2-$ | $NCH_3(C_2H_5)$ |
| 48. | $(CH_2)_2$ | $(CH_2)_4$ | $CO_2H$ | $(CH_2)_2$ | $-N(CH_3)_2$ |
| 49. | CH=CH | $-CH_2C(F)_2-$ | tetrazolyl (N-H) | $(CH_2)_3$ | $C_4H_9$ |

-continued

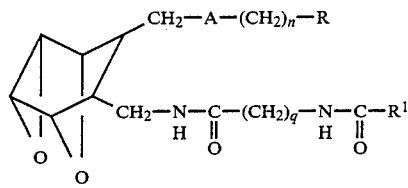

| Ex. No. | A | (CH₂)ₙ | R | (CH₂)q | R¹ |
|---|---|---|---|---|---|
| 50. | (CH₂)₂ | −CH₂−C(CH₃)(CH₃)− | CO₂H | −CH(F)−CH₂− | −NH−CH₂−C₆H₅ |
| 51. | CH=CH | (CH₂)₅ | CO₂H | −C(F)(F)−CH₂ | −(CH₂)₂CH=CHCH₃ |
| 52. | (CH₂)₂ | −CH(CH₃)−CH(F)− | CO₂H | (CH₂)₂ | C₆H₅ |
| 53. | (CH₂)₂ | (CH₂)₂ | (tetrazole) | CH₂ | −CH₂C₆H₅ |
| 54. | CH=CH | (CH₂)₃ | CO₂CH₃ | (CH₂)₃ | −SC₄H₉ |
| 55. | 2(CH₂)₂ | (CH₂)₄ | CO₂CH₃ | (CH₂)₈ | −SC₆H₅ |
| 56. | CH=CH | (CH₂)₅ | CO₂H | (CH₂)₁₀ | −NCH₃(C₆H₅) |
| 57. | CH=CH | CH₂ | CO₂H | (CH₂)₂ | C₂H₅ |
| 58. | (CH₂)₂ | (CH₂)₂ | CO₂H | (CH₂)₃ | CH₃ |
| 59. | CH=CH | (CH₂)₃ | (tetrazole) | (CH₂)₄ | −CH=CH−CH₃ |
| 60. | (CH₂)₂ | (CH₂)₄ | CO₂H | (CH₂)₅ | −C≡C−CH₃ |
| 61. | CH=CH | (CH₂)₅ | CO₂H | (CH₂)₆ | −CH₂−C≡C−CH₃ |
| 62. | CH=CH | (CH₂)₃ | CO₂H | CH₂ | −S(=O)C₆H₅ |
| 63. | CH=CH | CH₂ | CO₂H | CH₂ | −S(=O)(=O)C₂H₅ |
| 64. | (CH₂)₂ | (CH₂)₃ | CO₂H | (CH₂)₂ | −SCH₂C₆H₅ |
| 65. | CH=CH | (CH₂)₃ | CO₂H | (CH₂)₃ | −CH₂−S−C₂H₅ |
| 66. | (CH₂)₂ | (CH₂)₃ | CO₂H | CH₂ | −CH₂−S−CH₂−C₆H₅ |
| 67. | CH=CH | (CH₂)₃ | CO₂H | CH₂ | −CH₂−O−CH₂−C₆H₅ |
| 68. | CH=CH | CH₂ | CO₂H | CH₂ | −CH₂−N(H)−CH₂C₆H₅ |
| 69. | (CH₂)₂ | (CH₂)₃ | CO₂CH₃ | (CH₂)₂ | −CH₂−S−C₄H₉ |

What is claimed is:
1. A compound having the structure

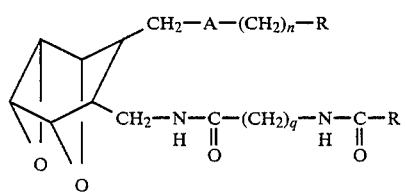

including all stereoisomers thereof, wherein A is —CH=CH— or —CH₂—CH₂—; n is 1 to 5; R is CO₂H, CO₂alkyl, CO₂ alkali metal, CO₂ polyhydroxyamine salt or (tetrazole);

q is 1 to 12; and $R^1$ is lower alkyl, lower alkenyl, lower alkynyl, aryl, arylalkyl, lower alkoxy, arylalkloxy, aryloxy, alkylamino, arylamino, arylalkylamino,

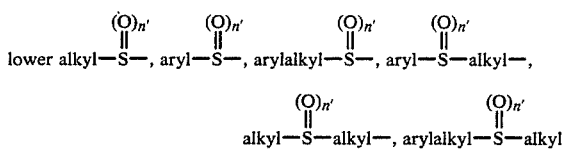

(wherein n' is 0, 1 or 2), alkylaminoalkyl, arylaminoalkyl, arylalkylaminoalkyl, alkoxyalkyl, aryloxyalkyl or arylakoxyalkyl, wherein lower alkyl or alkyl alone or as part of another group contains 1 to 12 carbons and is unsubstituted or is substituted with halo, $CF_3$, alkoxy, aryl, alkyl-aryl, haloaryl, cycloalkyl, alkylcyloalkyl, hydroxy, alkylamino, alkanoylamino, arylcarbonylamino, nitro, cyano, thiol or alkylthio; and aryl alone or as part of another group is a monocyclic or bicylic aromatic group containing from 6 to 10 carbons in the ring portion, and which is unsubstituted or is substituted with 1 or 2 lower alkyl groups, 1 or 2 halogens, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups; and cycloalkyl alone or as part of another group contains 3 to 12 carbons and is unsubstituted or is substituted with 1 or 2 halogens, 1 or 2 lower alkyl groups, 1 or 2 lower alkoxy groups, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

2. The compound as defined in claim 1 wherein $R^1$ is alkyl, alkoxy or arylthioalkyl.

3. The compound as defined in claim 1 wherein A is CH=CH.

4. The compound as defined in claim 1 wherein n is 2 to 4 and q is 1.

5. The compound as defined in claim 1 wherein R is $CO_2H$ or

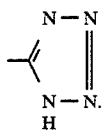

6. The compound as defined in claim 1 wherein n is 2 to 4, R is $CO_2H$, or

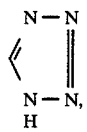

q is 1, and $R^1$ is alkyl, alkoxy or phenylthiomethyl.

7. The compound as defined in claim 1 having the name [1α,2β(Z),3β,4α,5α,6α]-7-[5,6-epoxy-3-[[[[(1-oxohexyl)amino]acetyl]amino]methyl]-7-oxabicyclo[2.2.1]hept-2-yl]-5-heptenoic acid or esters thereof, including all stereoisomers thereof.

8. The compound as defined in claim 1 having the name [1α,2β(Z),3β,4α,5α,6α]-7-[5,6-epoxy-3-[[[[(phenoxyacetyl)amino]acetyl]amino]methyl]-7-oxabicyclo[2.2.1]hept-2-yl]-5-heptenoic acid or esters thereof including all stereoisomers thereof.

9. The compound as defined in claim 1 having the name [1α,2β(5Z),3β,4α,5α,6α]-7-[5,6-epoxy-3-[[[[(1-oxo-3-phenylpropyl)amino]acetyl]amino]methyl]-7-oxabicyclo[2.2.1]hept-2-yl]-5-heptenoic acid or esters thereof including all stereoisomers thereof.

10. The compound as defined in claim 1 having the name [1α,2β(5Z),3β,4α,5α,6α]-7-[5,6-epoxy-3-[[[(1-oxo-5-phenylpentyl)amino]acetyl]amino]methyl]-7-oxabicyclo[2.2.1]hept-2-yl]-5-heptenoic acid or esters thereof including all stereoisomers thereof.

11. The compound as defined in claim 1 having the name [1α,2β(Z),3β,4α,5α,6α]-7-[5,6-epoxy-3-[[[[(4-cyclohexyl-1-oxobutyl)amino]acetyl]amino]methyl]-7-oxabicyclo[2.2.1]hept-2-yl]-5heptenoic acid or esters thereof including all stereoisomers thereof.

12. The compound as defined in claim 1 having the name [1α,2β(Z),3β,4α,5α,6α]-7-[5,6-epoxy-3-[[[[1-oxo-3-(phenylthio)propyl]amino]acetyl]amino]methyl]-7-oxabicyclo[2.2.1]hept-2-yl]-5-heptenoic acid or esters thereof including all stereoisomers thereof.

13. The compound as defined in claim 1 having the name [1α,2β(Z),3β,4α,5α,6α]-7-[5,6-epoxy-3-[[[[[(phenylmethyl)thio]acetyl]amino]acetyl]amino]methyl]-7-oxabicyclo[2.2.1]hept-2-yl]-5-heptenoic acid or esters thereof including all stereoisomers thereof.

14. The compound as defined in claim 1 having the name [1α,2β(Z),3β,4α,5α,6α]-7-[5,6-epoxy-3-[[[[(butylthio)acetyl]amino]acetyl]amino]methyl]-7-oxabicyclo[2.2.1]hept-2-yl]-5-heptenoic acid or esters thereof including all stereoisomers thereof.

15. The compound as defined in claim 1 having the name [1α,2β(Z),3β,4α,5α,6α]-7-[5,6-epoxy-3-[[[[[(cyclohexylmethyl)thio]acetyl]amino]acetyl]amino]methyl]-7-oxabicyclo[2.2.1]-hept-2-yl]-5-heptenoic acid or esters thereof including all stereoisomers thereof.

16. The compound as defined in claim 1 having the name [1α,2β(Z),3β,4α,5α,6α]-7-[5,6-epoxy-3-[[[[(phenylsulfinyl)acetyl]amino]acetyl] -amino]methyl]-7-oxabicyclo[2.2.1]hept-2-yl]-5heptenoic acid or esters thereof including all stereoisomers thereof.

17. The compound as defined in claim 1 having the name [1α,2β(Z),3β,4α,5α,6α]-7-[5,6-epoxy-3-[[[[(phenylsulfonyl)acetyl]amino]acetyl]amino]methyl]-7-oxabicyclo[2.2.1]hept-2-yl]-5-heptenoic acid or esters thereof including all stereoisomers thereof.

18. A method of inhibiting platelet aggregation and/or bronchoconstriction, which comprises administering to the circulatory system of a mammalian host an effective amount of a compound as defined in claim 1 or a pharmaceutically acceptable salt thereof.

19. The method as defined in claim 18 wherein said compound is administered in an amount within the range of from about 1 to about 100 mg/kg.

20. A composition for inhibiting platelet aggregation and/or bronchoconstriction comprising an effective amount of a compound as defined in claim 1 or a pharmaceutically acceptable salt thereof, and a pharmaceutically acceptable carrier therefor.

21. A method of treating peripheral vascular diseases, which comprises topically or systemically administering to a mammalian host an effective amount of a compound as defined in claim 1 or a pharmaceutically acceptable salt thereof.

* * * * *